(12) United States Patent
Byrd et al.

(10) Patent No.: US 8,318,812 B2
(45) Date of Patent: Nov. 27, 2012

(54) THERAPEUTIC AGENTS FOR THE TREATMENT OF LYMPHOID MALIGNANCIES

(75) Inventors: John C. Byrd, Arlington, OH (US); Danilo Perrotti, Dublin, OH (US); Ching-Shih Chen, Upper Arlington, OH (US); James T. Dalton, Lakeland, TN (US); Frank Frissora, Columbus, OH (US); Xiaobin Zhao, Columbus, OH (US); Qing Liu, Rockville, MD (US); Natarajan Muthusamy, Galloway, OH (US)

(73) Assignee: The Ohio State University Research Foundation, Columbus, OH (US)

(*) Notice: Subject to any disclaimer, the term of this patent is extended or adjusted under 35 U.S.C. 154(b) by 490 days.

(21) Appl. No.: 12/302,953

(22) PCT Filed: Jun. 1, 2007

(86) PCT No.: PCT/US2007/012921
§ 371 (c)(1), (2), (4) Date: May 1, 2009

(87) PCT Pub. No.: WO2007/143081
PCT Pub. Date: Dec. 13, 2007

(65) Prior Publication Data
US 2010/0022655 A1 Jan. 28, 2010

Related U.S. Application Data

(60) Provisional application No. 60/803,845, filed on Jun. 2, 2006.

(51) Int. Cl.
*A61K 31/135* (2006.01)
(52) U.S. Cl. ....... 514/653; 514/19.6; 514/183; 514/424; 435/7.21
(58) Field of Classification Search ............ 514/19.6, 514/183, 424; 435/7.21
See application file for complete search history.

(56) References Cited

U.S. PATENT DOCUMENTS

| | | | |
|---|---|---|---|
| 2,680,749 | A | 6/1954 | Cawley et al. |
| 4,262,017 | A | 4/1981 | Kulpers et al. |
| 4,751,224 | A | 6/1988 | Agarwal et al. |
| 4,938,949 | A | 7/1990 | Borch et al. |
| 6,004,565 | A | 12/1999 | Chiba et al. |
| 6,121,329 | A | 9/2000 | Fujii et al. |
| 6,417,223 | B1 | 7/2002 | Sanders et al. |
| 6,476,004 | B1 | 11/2002 | Sakai et al. |
| 6,645,998 | B2 | 11/2003 | Sanders et al. |
| 6,703,384 | B2 | 3/2004 | Sanders et al. |
| 6,770,672 | B1 | 8/2004 | Sanders et al. |
| 6,858,227 | B1 | 2/2005 | Lal et al. |
| 2004/0235938 | A1 | 11/2004 | Sanders et al. |
| 2004/0248971 | A1 | 12/2004 | Yeh et al. |
| 2005/0065149 | A1 | 3/2005 | Wang et al. |
| 2005/0090520 | A1 | 4/2005 | Lindquist |
| 2005/0215531 | A1* | 9/2005 | Baumruker et al. ......... 514/114 |
| 2008/0009545 | A1 | 1/2008 | Chen et al. |
| 2008/0161349 | A1 | 7/2008 | Sanders et al. |
| 2009/0137530 | A1 | 5/2009 | Masatoshi et al. |
| 2010/0179216 | A1 | 7/2010 | Masatoshi et al. |
| 2010/0267673 | A1 | 10/2010 | Chen et al. |
| 2010/0267820 | A1 | 10/2010 | Chen et al. |
| 2010/0273871 | A1 | 10/2010 | Chen et al. |

FOREIGN PATENT DOCUMENTS

| | | |
|---|---|---|
| JP | 59-222415 | 12/1984 |
| WO | 01/58889 | 8/2001 |
| WO | 03/039461 | 5/2003 |
| WO | 2007/098139 | 8/2007 |
| WO | 2007/143081 | 12/2007 |
| WO | 2008/021532 | 2/2008 |
| WO | 2010/042998 | 4/2010 |
| WO | 2010/120711 | 10/2010 |
| WO | 2010/121111 | 10/2010 |

OTHER PUBLICATIONS

Suzuki et al., "A new immunosuppressant, FTY720, induces bcl-2-associated apoptotic cell death in human lymphocytes", Immunology, 89: 518-523 (1996).
Enosawa et al., "Induction of selective cell death targeting on mature T-lymphocytes in rats by a novel immunosuppressant, FTY720", Immunopharmacology, 34: 171-179 (1996).
Budde et al., "Pharmacodynamics of single doses of the novel immunosuppressant FTY720 in stable renal transplant patients", American Journal of Transplantation; 3: 846-854 (2003).
Brinkmann et al., "FTY720: sphingosine 1-phosphate receptor-1 in the control of lymphocyte egress and endothelial barrier function", American Journal of Transplantation; 4: 1019-1025 (2004).
Brinkmann, V. "FTY720: mechanism of action and potential benefit in organ transplantation", Yonsei Medical Journal, 45: 991-997 (2004).
Pabst et al., "Enhanced FTY720-mediated lymphocyte homing requires G alpha i signaling and depends on beta 2 and beta 7 integrin", J. Immunol, 176: 1474-1480 (2006).
Bohler et al., "FTY720 mediates apoptosis-independent lymphopenia in human renal allograft recipients: different effects on CD62L+ and CCR5+ T lymphocytes", Transplantation, 77: 1424-1432 (2004).

(Continued)

*Primary Examiner* — James D Anderson
*Assistant Examiner* — Ibrahim D Bori

(57) ABSTRACT

Methods—for treatment and prevention of lymphoid malignancies, including, but not limited to acute lymphoblastic leukemia (ALL), chronic lymphocytic leukemia (CLL), B-cell lymphoma, Acute Myeloid leukemia (AML), and mantle cell lymphoma (MCL). The methods include administration of a therapeutically effective amount of FTY720 (2-Amino-2-[2-(4-octylphenyl)ethyl]propane 1,3-diol hydrochloride) or a derivative, pharmaceutically acceptable salt thereof, or a prodrug thereof to a subject.

11 Claims, 15 Drawing Sheets

OTHER PUBLICATIONS

Brinkmann, V., "FTY720 alters lymphocyte homing and protects allografts without inducing general immunosuppression", Transplantation Proceedings, 33: 530-531 (2001).
Brinkmann et al., "The immune modulator FTY720 targets sphingosine 1-phosphate receptors", The Journal of Biological Chemistry, 277: 21453-21457 (2002).
Brinkmann, et al., "FTY720: targeting G-protein-coupled receptors for sphingosine 1-phosphate in transplantation and autoimmunity", Current Opinion in Immunology, 14: 569-575 (2002).
Nagahara et al., "Coordinate involvement of cell cycle arrest and apoptosis strengthen the effect of FTY720", Japanese Journal of Cancer Research : 92: 680-687 (2001).
Matsuoka et al, "A novel immunosuppressive agent FTY720 induced Akt dephosphorylation in leukemia cells", British Journal of Pharmacology, 138: 1303-1312 (2003).
Nagahara et al., "T cell selective apoptosis by a novel immunosuppressant, FTY720, is closely regulated with Bcl-2", British Journal of Pharmacology, 137: 953-962 (2002).
Quesniaux et al, "The novel immunosuppressant FTY720 induces peripheral lymphodepletion of both T- and B-cells in cynomolgus monkeys when given alone, with Cyclosporine Neoral (R) or with RAD", Transplant Immunology, 8: 177-187 (2000).
Nagahara et al., "Evidence that FTY720 induces T cell apoptosis in vivo", Immunopharmacology, 48: 75-85 (2000).
Li et al., "Induction of lymphocyte apoptosis by a novel immunosuppressant FTY720: relation with Fas, Bcl-2 and Bax expression", Transplantation Proceedings, 29: 1267-1268 (1997).
Yasui et al., "FTY720 induces apoptosis in multiple myeloma cells and overcomes drug resistance", Cancer Research, 65: 7478-7484 (2005).
Kitada et al. "Expression of apoptosis-regulating proteins in chronic lymphocytic leukemia: correlations with In vitro and In vivo chemoresponses", Blood, 91: 3379-3389 (1998).
Fujino, et al., "Activation of caspases and mitochondria in FTY720-mediated apoptosis in human T cell line Jurkat", International Immunopharmacology, 1: 2011-2021 (2001).
Morley et al., "Proteasome inhibitors and immunosuppressive drugs promote the cleavage of eIF4GI and eIF4GII by caspase-8-independent mechanisms in Jurkat T cell lines" FEBS Letters, 503: 206-212 (2001).
Bohler et al., "Pharmacodynamics of FTY720, the first member of a new class of immune-modulating therapeutics in transplantation medicine", International Journal of Clinical Pharmacology and Therapeutics, 41: 482-487 (2003).
Chua et al., "FTY720, a fungus metabolite, inhibits in vivo growth of androgen-independent prostate cancer", International Journal of Cancer, 117: 1039-1048 (2005).
Zhou et al., "FTY720, a fungus metabolite, inhibits invasion ability of androgen-independent prostate cancer cells through inactivation of RhoA-GTPase", Cancer Letters, 233: 36-47 (2006).
Azuma et al., "Marked prevention of tumor growth and metastasis by a novel immunosuppressive agent, FTY720, in mouse breast cancer models", Cancer Research, 62: 1410-1419 (2002).
Azuma et al. "Selective cancer cell apoptosis induced by FTY720; evidence for a Bcl-dependent pathway and impairment in ERK activity", Anticancer Research, 23: 3183-3193 (2003).
Lee et al., "Significance of the Rac signaling pathway in HCC cell motility: implications for a new therapeutic target", Carcinogenesis, 26: 681-687 (2005).
Lee et al., "FTY720: a promising agent for treatment of metastatic hepatocellular carcinoma. Clinical Cancer Research : an Official Journal of the American Association for Cancer Research", 11: 8458-8466 (2005).
Lee et al., "FTY720 induces apoptosis of human hepatoma cell lines through PI3-K-mediated Akt dephosphorylation", Carcinogenesis, 25: 2397-2405 (2004).
Ho et al., "Effects of a novel immunomodulating agent, FTY720, on tumor growth and angiogenesis in hepatocellular carcinoma", Molecular Cancer Therapeutics, 4: 1430-1438 (2005).
International Search Report for PCT/US2006/010882, mailed Feb. 9, 2007.
International Search Report for PCT/US07/12921, mailed Dec. 12, 2007.
Johnson et al., "A novel celecoxib derivative, OSU03012, induces cytotoxicity in primary CLL cells and transformed B-cell lymphoma cell line via a caspase- and Bcl-2-independent mechanism", Blood, v.105, p. 2504-2509 (2005).
Li et al., "The myeloid leukemia-associated protein SET is a potent inhibitor of protein phosphatase 2A", J. Biol. Chem. 271, pp. 11059-11062 (1996).
Feschenko et al., "A novel cAMP-stimulated pathway in protein phosphatase 2A activation", J. Pharmacol. Exp. Ther. 302, pp. 111-118 (2002).
Moon et al., "PDE4 inhibitors activate a mitochondrial apoptotic pathway in chronic lymphocytic leukemia cells that is regulated by protein phosphatase 2A", Blood 101, pp. 4122-4130 (2003).
Schonthal, A. H., "Role of serine/threonine protein phosphatase 2A in cancer", Cancer Lett. 170, pp. 1-13 (2001).
Salesse et al., "BCR/ABL-mediated increased expression of multiple known and novel genes that may contribute to the pathogenesis of chronic myelogenous leukemia", Molecular Cancer Therapeutics, v. 2, p. 173-182 (2003).
Fujino et al., "Distinct pathways of apoptosis triggered by FTY720, etoposide, and anti-Fas antibody in human T-lymphoma cell line (Jurkat cells)", Journal of Pharmacology and Experimental Therapeutics, 300, p. 939-945 (2002).
Li Dengju et al., "Role of extracellular regulated protein kinases in FTY720-induced apoptosis of leukemia cell lines HL-60 and U937", Journal of Huazhong University of Science and Technology [Med Sci], 24, p. 45-47 (2004).
Nagahara et al., "Immunosuppressant FTY720 induces apoptosis by direct induction of permeability transition and release of cytochrome c from mitochondria", Journal of Immunology, 165, p. 3250-3259 (2000).
Matsuoka et al., "Reduction of phosphorylated Akt/PKB by immunosuppressant FTY720" Cell Biology International, 24, p. 976-977 (2000).
Seitz et al., "Effects of sphingosine 1-phosphate (S1P) and expression of S1P receptors in chronic lymphocyte leukemia (B-CLL): potential role in cell trafficking and survival", 33, p. 99 (2005).
Extended European Search Report for EP 07809273, Mailed Aug. 14, 2009.
Qian et al., "c-Jun involvement in vitamin E succinate induced apoptosis of reticuloendothellosis virus transformed avian lymphoid cells", Oncogene 15, pp. 223-230 (1997).
Reno et al., "Analysis of protein kinase C delta (PKCδ) expression in endometrial tumors", Hum Pathol, 39, pp. 21-29 (2008).
Reyland, "Protein kinase Cδ and apoptosis", Biochem Soc Trans 35, pp. 1001-1004 (2007).
Roberts et al., "Antitumor activity and pharmacology of a selective focal adhesion kiriase inhibitor, PF-562,271", Cancer Res 68. pp. 1935-1944 (2008).
Schmidmaier et al., Curr Med Chem 15, pp. 978-990 (2008).
Zolnierowicz, S., "Type 2A protein phosphatase, the complex regulator of numerous signaling pathways", Biochem Pharmacol, 60: pp. 1225-1235 (2000).
Shanker et al., "Vitamin E succinate in combination with mda-7 results in enhanced human ovarian tumor cell killing through modulation of extrinsic and intrinsic apoptotic pathways", Cancer Lett, 254, pp. 217-226 (2007).
Shiau et al., "Thiazolidenediones mediate apoptosis in prostate cancer cells in part through inhibition of Bcl-xL/Bcl-2 functions independently of PPAR", Cancer Res 65, pp. 1561-1569 (2005).
Shiau et al., "a-tocopheryl succinate induces apoptosis in prostate cancer cells in part through inhibition of Bcl-xL/Bcl-2 function", J Biol Chem, 281, pp. 11819-11825 (2006).
Skerjanec et al., "FTY720, a novel immunomodulator in de novo kidney transplant patients: pharmacokinetics and exposure-response relationship. Journal of Clinical Pharmacology, 45: 1268-1278, 2005".
Stoetzer et al., "Drug-induced apoptosis in chronic lymphocytic leukemia. Leukemia : Official Journal of the Leukemia Society of America, Leukemia Research Fund, U.K, 13: 1873-1880, 1999".

Suleiman at al., "FTY720 prevents renal T-cell infiltration after ischemia/reperfusion injury. Transplantation Proceedings, 37: 373-374, 2005".
Suzuki at al., "A novel immunosuppressant FTY720, with a unique mechanism of action, induces long-term graft acceptance in rat and dog allotransplantation", Transplantation, 61: pp. 200-205 (1996).
Suzuki et al., "Long-term graft acceptance in allografted rats and dogs by treatment with a novel immunosuppressant, FTY72O. Transplantation Proceedings, 28: 1375-1376, 1996."
Suzuki et al., "Induction of lymphocyte apoptosis and prolongation of allograft survival by FTY720. Transplantation Proceedings, 28: 2049-2050, 1996.".
Suzuki at ai., "Immunosuppressive effect of a new drug, FTY720, on lymphocyte responses in vitro and cardiac allograft survival in rats. Transplant Immunology, 4: 252-255, 1996."
Takabe et al., "Inside-out signaling of sphingosine-1-phosphate: therapeutic targets", Pharmacol Rev. 60, pp. 181-195 (2008).
Tchou et al., "GSTP1 CpG island DNA hypermethylation in hepatocellular carcinomas", Int J Onjcol, 16, pp. 663-676 (2000).
Tedesco-Silva et al., "FTY720, a novel imrnunomodulator: efficacy and safety results from the first phase 2A study in de novo renal transplantation. Transplantation, 77: 1826-1833, 2004.".
Tedesco-Silva et al., FTY720, a novel immunomodulator efficacy and safety results from the first phase 2A study in de novo renal transplantation. Transplantation, 79: 1553-1560, 2005.
Zhao et al., "alpha-tocopheryl succinate-induced apoptosis in human gastric cancer cells is modulated by ERK1/2 and c-Jun N-terminal kinase in a biphasic manner", Cancer Lett, 247, pp. 345-352 (2007).
Thomas, et al., "Drug-Induced apoptosis in B-cell chronic, lymphocytic leukemia: relationship between p53 gene mutation and bcl-2/bax proteins in drug resistance", Oncogene 12: pp. 1055-1062 (1996).
Thomas, et al., "Opportunities for Targeted Therapies in Hepatocellular carcinoma", J. Clin Oncol. 23, pp. 8093-8108 (2005).
Traber et al., "Vitamin E in humans: Demand and delivery", Annual Review of Nutrition, vol. 16, pp. 321-347, Jul. 1996.
Tseng et al., "Overcoming trastuzumab resistance in HER2-overexpressing breast cancer cells by using a novel celecoxib-derived phosphoinositide-dependent kinase-1 inhibitor", Mol Pharmacol 70, pp. 1534-1541 (2006).
Van Assche et al., "Physiological basis for novel drug therapies used to treat the inflammatory bowel diseases. I. Immunology and therapeutic potential of antiadhesion molecule therapy in inflammatory bowel disease", Am J Physiol Gastrointest Liver Physiol, 288, pp. G169-G174 (2005).
Varga at al., "Tumor grade-depdneent alterations in the protein kinase C isoform pattern in urinary bladder carcinomas", Eur Urol 46, pp. 462-465 (2004).
Zhang et al., "Vitamin E succinate inhibits the function of androgen receptor and the expression of prostate-specific antigen in prostate cancer cells", Proc Natl Acad Sci USA, 99, pp. 7408-7413 (2002).
Wang et al., "Vitamin E analogues as anticancer agents: lessons from studies with alpha-tocopheryl succinate", Mol. Nutr. Food Res., 50, pp. 675-685 (2006).
Wang et al., "Repression of androgen receptor in prostate cancer cells by phenethyl isothiocyanate", Carcinogenesis, 27, pp. 2124-2132 (2006).
Wang et al., "A peptide conjugate of vitamin E succinate target breast cancer cells with high ErbB2 expression", Cancer Res 67, pp. 3337-3344 (2007).
Wang et al., "a-Tocopheryl succinate as a scaffold to develop potent inhibitors of breast cancer cell adhesion", J Med Chem 52, pp. 5642-5648 (2009).
Weber et al., "Induction of cancer cell apoptosis by alpha-tocopheryl succinate: molecular pathways and structural requirements", FASEB, J., 15 (2) Feb. 2001.
Weber et al., "Vitamin E succinate is a potent novel antineoplastic agent with high selectivity and cooperativity with tumor necrosis factor-related apoptosis-inducing ligang (Apo2 ligand) in vivo", Clin Cancer Res 8, pp. 863-869 (2002).
Weber et al., "Mitochondria play a central role in apoptosis induced by alpha-tocopheryl succinate, an agent with antineoplastic activity: comparison with receptor-mediated pro-apoptotic signaling", Biochemistry, 42, pp. 4277-4291 (2003).
Yusof et al., "Immunohistochemical expression of π class glutathione S-transferase and α-Fetoprotein in hepatocellular carcinoma and chronic liver disease", Anal Quant Cytol Histol, 25, pp. 332-338 (2003).
Wu et al., "Cellular and molecular effects of alpha-tocopheryloxybutyrate: Lessions for the design of vitamin E analog for cancer prevention", Anticander Research, Helenic Anticancer Institute, Athens, vol. 24, No. 6, Nov. 1, 2004 pp. 3795-3802.
Yang et al., "Bcl-xL mediates a survival mechanism independent of the phosphoinositide 3-Kinase/Akt pathway in prostate cancer cells", J Biol Chem 278, pp. 25872-25878 (2003).
Yu et al., "Activation of extracellular signal-regulated kinase and c-Jun-NH(2)-terminal kinase but not p38 mitogen-activated protein kinases is required for RRR-alpha-tocopheryl succinate-induced apoptosis of human breast cancer cells", Cancer Res 61, pp. 6569-6576 (2001).
Yin et al., "The therapeutic and preventive effect of RRR-alpha-vitamin E succinate on prostate cancer via induction of insulin-like growth factor binding protein-3", Clin Cancer Res, 13, pp. 2271-2280 (2007).
You et al., "Role of extracellular signal-regulated kinase pathway in RRR-alpha-tocopheryl succinate-induced differentiation of human MDA-MB-435 breat cancer cells", Mel Carcinog, 33, pp. 228-236 (2002).
You et al., "RRR-alpha-tocopheryl succinate induces MDA-MB-435 and MCF-7 human breast cancer cells to undergo differentiation", Cell Growth Differ, 12, pp. 471-480 (2001).
Ferguson, R., "FTY720 immunomodulation: optimism for improved transplant regimens. Transplantation Proceedings, 36: 549S-553S, 2004".
Genini et al., "Nucleotide requirements for the in vitro activation of the apoptosis protein-activating factor-1-mediated caspase pathway. The Journal of Biological Chemistry, 275: 29-34, 2000".
Prieschl, "The balance between sphingosine and sphingosine-1-phosphate is decisive for mast cell activation after Fœ receptor I triggering", J Exp Med 190, pp. 1-8 (1999).
Gu et al., "Vitamin E succinate induces ceramide-mediated apoptosis in head and neck squamous cell carcinoma in vitro and in vivo", Clin Cancer Res, 14, pp. 1840-1848 (2008).
Hahn et al., "Dietary administration of the proapoptotic vitamin E analogue alpha-tocopheryloxyacetic acid inhibits metastatic murine breast cancer", Cancer Res 66, pp. 9374-9378 (2006).
Haynes et al., J Pharm Sci, 94, pp. 2111-2120 (2005).
Omar et al., "Targeting of the Akt-nuclear factor-κB signaling network by [1-(4-chloro-3-nitrobenzenesulfonyl)-1H-indol-3-yl]-methanol (OSU-A9), a novel indole-3-carbinol derivative, in a mouse model of hepatocellular carcinoma", Mol Pharmacol 76, pp. 957-968 (2009).
Hoshino et al., "FTY720, a novel immunosuppressant possessing unique mechanims. II. Long-term graft survival induction in rat heterotopic cardiace allografts and synergistic effect in combination with cyclosporine A", Transplantation Proceedings, 28: pp. 1060-1061 (1996).
Huang et al., "a-Tocopheryl succinate and derivatives mediate the transcriptional repression of androgen receptor in prostate cancer cells by targeting the PP2A-JNK-Sp1 Signaling axis", Carcinogenesis, vol. 30, No. 7, pp. 1125-1131, 2009.
Hung et al., FTY720 induces apoptosis in hepatocellular carcinoma cells through activation of protein kinase Cδ signaling, Cancer Res 68, pp. 1204-1212 (2008).
Jackson et al., "The enigmatic protein kinase Cδ: complex roles in cell proliferation and survival", FASEB J, 18, pp. 627-636 (2004).
Janssens et al., "Protein phosphatase 2A: a highly regulated family of serine/threonine phosphatases implicated in cell growth and signalling", Biochem J, 353, pp. 417-439 (2001).
Juntilla et al., "CIP2A inhibits PP2A in human malignancies", Cell, 130, pp. 51-62 (2007).
Kahan et al., "Pharmacodynamics, pharmacokinetics, and safety of multiple doses of FTY720 in stable renal transplant patients: a multicenter, randomized, placebo-controlled, phase I study. Transplantation, 76: 1079-1084, 2003".

Kawaguchi et al., "FTY720, a novel immunosuppressant possessing unique mechanisms. III. Synergistic prolongation of canine renal allograft survival in combination with cyclosporine A", Transplantation Proceedings 28: pp. 1062-1063 (1996).

Prasad et al., "Effects of tocopherol (Vitamin E) acid succinate on morphological alterations and growth inhibition in melanoma cells in culture", Cancer Res 42, pp. 550-555 (1982).

Kiuchi et al., "Synthesis and immunosuppressive activity of 2-substituted 2-aminopropane-1, d-diols and 2-aminoethanols", J Med Chem 43, pp. 2946-2961 (2000).

Kogure et al., "Potentiation of anti-cancer effect by intravenous administration of vesiculated tocophyeryl hemisuccinate on mouse melanoma in vivo", Cancer Lett, 192, pp. 19-24 (2003).

Koopman et al., Annexin V for flow cytometric detection of phosphatidylserine expression on B cells undergoing apoptosis. Blood, 84: 1415-1420, 1994.

Lawson et al., "Novel vitamin E analogue decreases syngeneic mouse mammary tumor burden and reduces lung metastasis", Mol Cancer Ther, 2, pp. 437-444 (2003).

Lei et al., "The Bax subfamily of Bcl2-related proteins is essential for apoptotic signal transduction by c-Jun NH(2)-terminal kinase", Mol Cell Biol, 22, pp. 4929-4942 (2002).

Prasad et al., "a-Tocopheryl succinate, the most effective form of vitamin E for adjuvant cancer treatment: A review", J Am Coll Nutr 22, pp. 108-117 (2003).

Liu, "Small molecule antagonists of LFA-1/ICAM-1 interactions as potential therapeutic agents", Expert Opinion Ther. Patents, 11 (9): pp. 1383-1393 (2001).

Llovet et al., "Sorafenib in advanced hepatocellular carcinoma", N Engl J Med, 359, pp. 378-390 (2008).

Lockwood et al., "Anti-adhesion molecule therapy as an interventional strategy for autoimmune inflammation", Clin Immunol, 93, pp. 93-106 (1999).

Lugovskoy et al., "A Novel approach for characterizing protein ligand complexes: Molecular basis for specificity of small-molecule Bcl-2 inhibitors", J Am Chem Soc, 124, pp. 1234-1240 (2002).

Malafa et al., "Vitamin E succinate promotes breast cancer tumor dormancy", J Surg Res, 93, pp. 163-170 (2000).

Malafa et al., "Inhibition of angiogenesis and promotion of melanoma dormancy by vitamin E succinate", Ann Surg Oncol 9, pp. 1023-1032 (2002).

Martin, R., "Closing in on an oral treatment" Multiple Sclerosis, Nature 464, pp. 360-362 (2010).

Masubuchi et al., "FTY720, a novel immunosuppressant, possessing unique mechanisms. IV. Prevention of graft versus host reactions in rats. Transplantation Proceedings, 28: 1064-1065, 1996".

McLean et al., "The role of focal-adhesion kinase in cancer—a new therapeutic opportunity", Nat Rev Cancer 5, pp. 505-515 (2005).

McConkey, et al., "Apoptosis sensitivity in chronic lymphocytic leukemia is detrmined by endogenous endonuclease content and relative expression of BCL-2 and BAX", J. Immunol. 156: pp. 2624-2630 (1996).

Mitra et al., "Integrin-regulated FAK-Src signaling in normal and cancer cells", Curr Opin Cell Biol 18, pp. 516-523 (2006).

Mitra et al., "Focal adhesion kinase: in command and control of cell motility", Nat Rev Mol Cell Biol, 6, pp. 56-68 (2005).

Mullershausen et al., "Persistent signaling induced by FTY720-phosphate is mediated by internalized S1P1 receptors", Nat Chem Biol 5, pp. 428-434 (2009).

Mumby, M., "PP2A: unveiling a reluctant tumor suppressor", Cell, 130, pp. 21-24 (2007).

Neuzil et al., "a-Tocopheryl succinate-induced apoptosis in Jurkat T cells involves caspase-3 activation, and both lysosomal and mitochondrial destabilisation", FEBS Lett, 445, pp. 295-300 (1999).

Neuzil et al., "Induction of cancer cell apoptosis by alpha-tocopheryl succinate: molecular pathways and structural requirements", FASEB J, 15, pp. 403-415 (2001).

Neuzil et al., "Selective cancer cell killing by tocopheryl succinate", Br. J. Cancer, 84, pp. 87-89 (2001).

Neuzil et al., "a-Tocopheryl succinate epitomizes a compound with a shift in biological activity due to pro-vitamin-to-vitamin conversion", Biochem Biophys Res Commun, 293, pp. 1309-1313 (2002).

Neuzil et al., "Vitamin E analogs, a novel group of "mitocans," as anticancer agents: the importance of being redox-silent", Mol Pharmacol, 71: pp. 1185-1199 (2007).

Ni et al., "Vitamin E succinate inhibits human prostate cancer cell growth via modulating cell cycle regulatory machinery", Biochem Biophys Res Commun, 300, pp. 357-363 (2003).

International Search Report and Written Opinion from PCT/US07/04337 dated Sep. 19, 2008.

International Search Report and Written Opinion from PCT/US07/12921 dated Dec. 12, 2007.

International Search Report and Written Opinion from PCT/US10/30799 dated May 18, 2010.

International Search Report and Written Opinion from PCT/US10/31363 dated Jul. 13, 2010.

Interview Summary from U.S. Appl. No. 11/708,792 dated Apr. 9, 2009.

Office action from U.S. Appl. No. 11/708,792 dated Jul. 6, 2009.

Response to Office action from U.S. Appl. No. 11/708,792 dated Aug. 12, 2009.

Office action from U.S. Appl. No. 11/708,792 dated Nov. 27, 2009.

Notice of Abandonment from U.S. Appl. No. 11/708,792 dated Jun. 22, 2010.

Office action from U.S. Appl. No. 12/761,504 dated Apr. 11, 2012.

Office action from Australian Application No. 2007217810 dated Aug. 16, 2011.

Communication from European Application No. 07751119.4 dated Mar. 13, 2009.

Response from European Application No. 07751119.4 dated Feb. 17, 2010.

Response to European Communication from 07809273.1 dated Sep. 22, 2010.

Arya P., et al., "Design and Synthesis of Analogs of Vitamin E: Antiproliferative Activity Against Human Breast Andenocarcinoma Cells", Bioorganic & Medicinal Chemistry Letters, vol. 8, 1998, pp. 2433-2438.

Ayllon et al., "Protein phosphatase 1 alpha is a Ras-activated Bad phosphatase that regulated interleukin-2 deprivation-induced apoptosis", The EMBO Journal, 19, pp. 2237-2246 (2000).

Bakin et al., "Attenuation of Ras signaling restores androgen sensitivity to hormone-refractory C4-2 prostate ancer cells", Cancer Res. 63, pp. 1975-1980 (2003).

Bang et al., "Activation of PKC but not of ERK is required for vitamin E-succinate-induced apoptosis of HL-60 cells", Biochem Biophys Res. Commun, 288, pp. 789-797 (2001).

Barnett, et al., "Vitamin E succinate inhibits colon cancer liver metastases", J Surg Res 106, pp. 292-298 (2002).

Baumhoer et al., "Glypican 3 expression in human nonneoplastic, preneoplastic, and neoplastic tissues", Am J Clin Pathol, 129, pp. 899-906 (2008).

Bellosillo et al., "Involvement of CED-3/ICE proteases in the apoptosis of B-chronic lymphocytic leukemia cells", Blood, 89: 3378-3384 (1997).

Birringer et al., "Vitamin E analogues as inducers of apoptosis: structure-function relation", Br J Cancer 88, pp. 1948-1955 (2003).

Boehler et al., "FTY720 alters the composition of T-lymphocyte subpopulations in the peripheral blood compartment of renal transplant patients", Transplantation Proceedings, 34: 2242-2243 (2002).

Braun, W.E, "Renal transplantation: basic concepts and evolution of therapy. J Clin Apher, 18: 141-152, 2003.".

Budde et al., First human trial of FTY720, a novel immunomodulator, in stable renal transplant patients. Journal of the American Society of Nephrology : JASN, 13: 1073-1083, 2002.

Calabresi, et al., "Section IX Chemotherapy of Neoplastic Diseases—Introduction", Goodman & Gilman's The Pharmacological Basis of Theapeutics 10th ed, Hardman, et al., Eds, McGraw-Hill, NY, pp. 1381, 1383-1385 and 1388, (2001).

Carbrera et al., "Review article: the management of hepatocellular carcinoma", Aliment. Pharmacol. Ther. 31, pp. 461-476 (2010).

Cattan, et al., "The C.B.17 scid mouse strain as a model for human disseminated leukaemia and myeloma in vivo. Leukemia Research, 18: 513-522, 1994".

Cheson et al., "National Cancer Institute-sponsored Working Group guidelines for chronic lymphocytic leukemia: revised guidelines for diagnosis and treatment. Blood, 87: 4990-4997, 1996".

Cheson et al., "Myelodysplastic syndromes standardized response criteria: further definition. Blood, 98: 1985, 2001".

Chiang et al., "Protein phosphatase 2A acivates the proapoptotic function of BAD in interleukin- 3-dependent lymphoid cells by a mechanism requiring 14-3-3 dissociation", Blood, 1289-1297 (2001).

Chiba et al., "FTY720, a novel immunosuppressant possessing unique mechanisms. I. Prolongation of skin allograft survival and synergistic effect in combination with cyclosporine in rats", Transplantation Proceedings, 28, pp. 1056-1059 (1996).

Chuang et al., "Phosphorylation by c-Jun NH2-terminal kinase 1 regulates the stability of transcription factor Sp1 during mitosis", Mol Biol Cell 19, pp. 1139-1151 (2008).

Chueh et al., "Induction of tolerance toward rat cardiac allografts by treatment with allochimeric class I MHC antigen and FTY720. Transplantation, 64: 1407-1414, 1997".

Chrispen et al., "Vitamin E succinate inhibits NF-kappaB and prevents the development of a metastatic phenotype in prostate cancer cells: implications for chemoprevention", Prostate, 67, pp. 582-590 (2007).

Cohen et al., "Oral fingolimod or intramuscular interferon for relapsing multiple sclerosis", N Engl J Med 362, pp. 402-415 (2010).

D'Costa et al., "The proapoptosis tumor suppressor protein kinase C-δ is lost in human squamous cell carcinomas", Oncogene 25, pp. 378-386 (2006).

Dalen et al., "Alpha-tocopheryl succinate sensitises a T lymphoma cell line to TRAIL-induced apoptosis by suppressing NF-kappB activation", Br. J Cancer 88, pp. 153-158 (2003).

Degterev et al., "Identification of small-molecule inhibitors of interaction between the BH3 domain and Bcl-x", Nat. Cell Biol, 3, pp. 173-182 (2001).

Dong et al., "Vitamin E analogues inhibit angiogenesis by selective induction of apoptosis in proliferating endothelial cells: the role of oxidative stress", Cancer Res 67, pp. 11906-11913 (2007).

Dragun et al., "FTY720: early clinical experience. Transplantation Proceedings, 36: 544S-548S, 2004".

Dragun et al., "FTY720-induced lymphocyte homing modulates post-transplant preservation/reperfusion injury", Kidney Int 65, pp. 1076-1083 (2004).

Webster's online: http://www.merriam-webster.com/dictionary/trunctaed, accessed Nov. 17, 2009.

"Chem 30C Spring 2006 Handout", http://voh.chem.ucla.edu/vohtar/spring06/classes/30C/pdf/30chd3.pdf, online.

Database Beilstein, Beilstein Institute for Organic Chemistry, XP002519217, Database accession No. BRN:310616 & J American Chemical Society, No. 64, pp. 1082 (1942).

Database Beilstein, Beilstein Institute for Organic Chemistry, XP 002519218, Database accession No. BRN:276496, Helvetica Chimica Acta, vol. 21, p. 1622, 1938.

International Search Report and Written Opinion from PCT/US11/62304 dated Jun. 28, 2012.

Search Report from European Application No. 10765245.5 dated Jul. 11, 2012.

Search Report from European Application No. 07809273.1 dated Jun. 22, 2012.

* cited by examiner

*a.*

*b.*

*c.*

*a.*  *b.*

*c.*

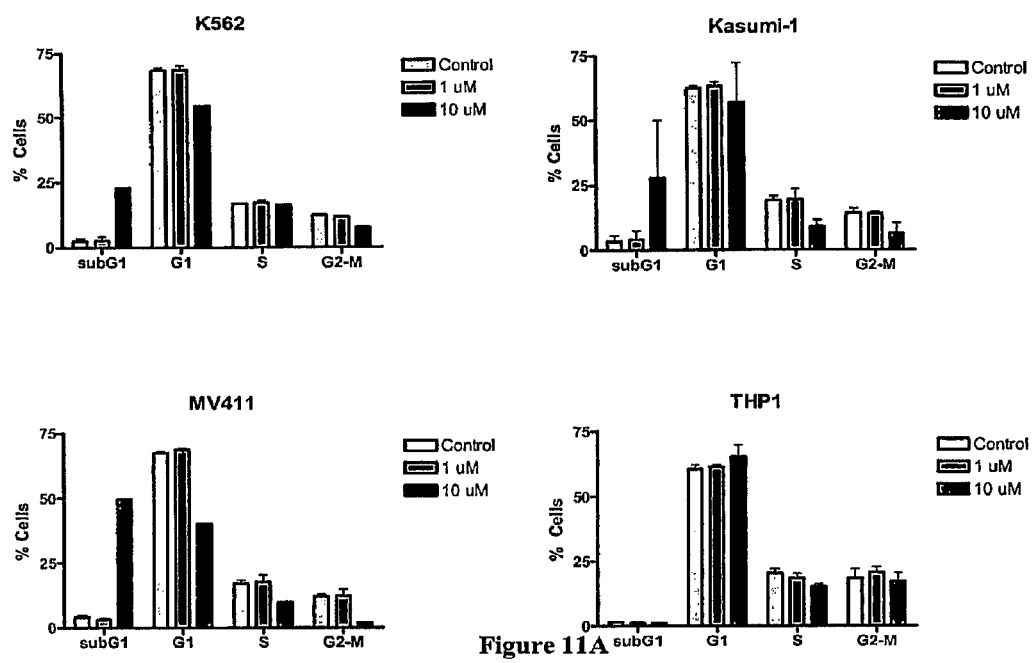
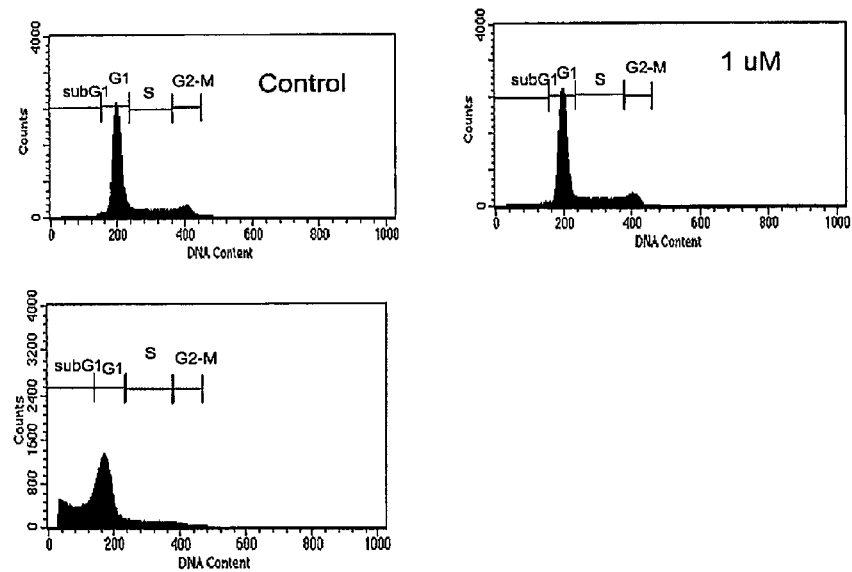
Figure 11A
Figure 11B

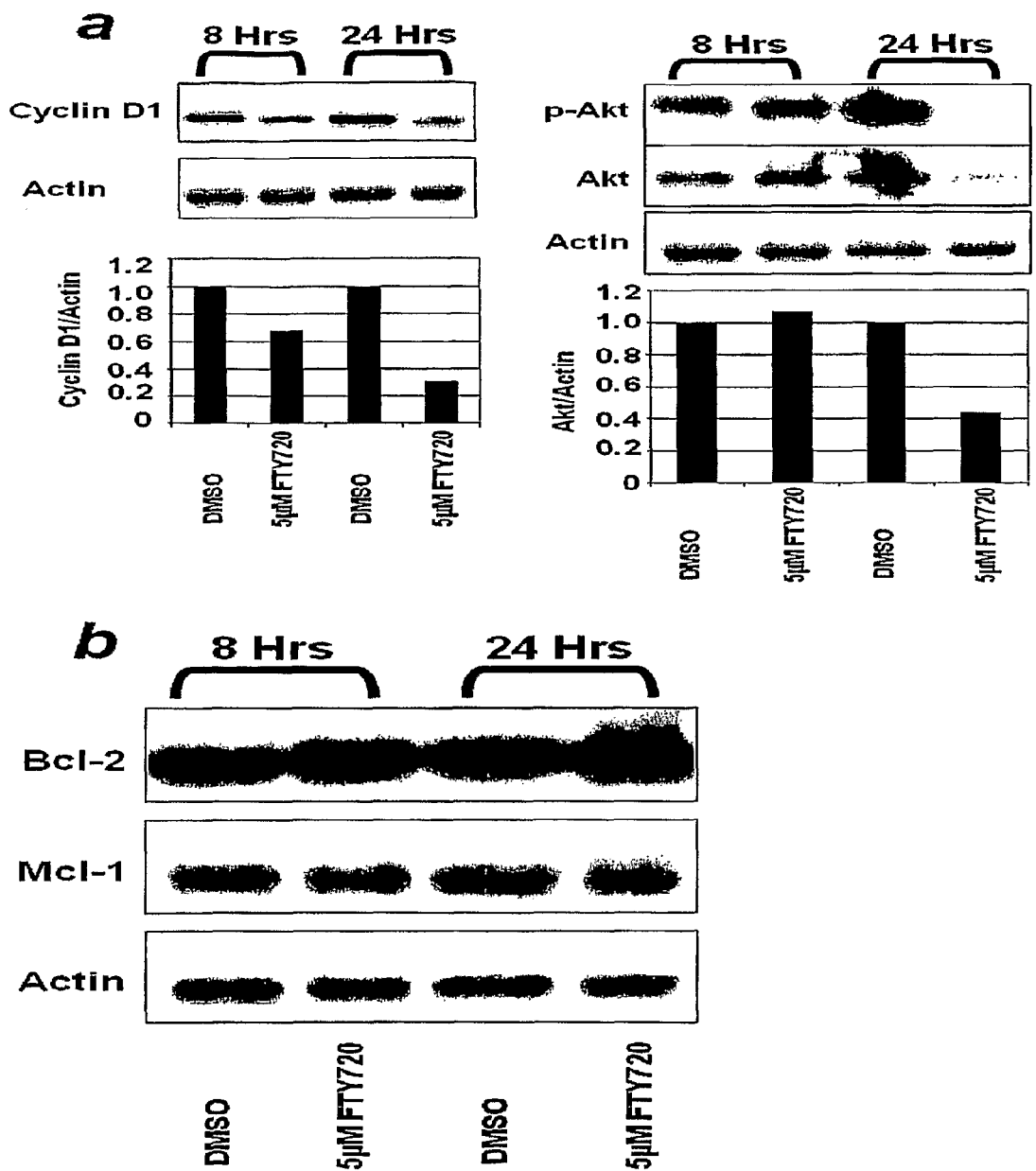
Figure 14 (a, b)

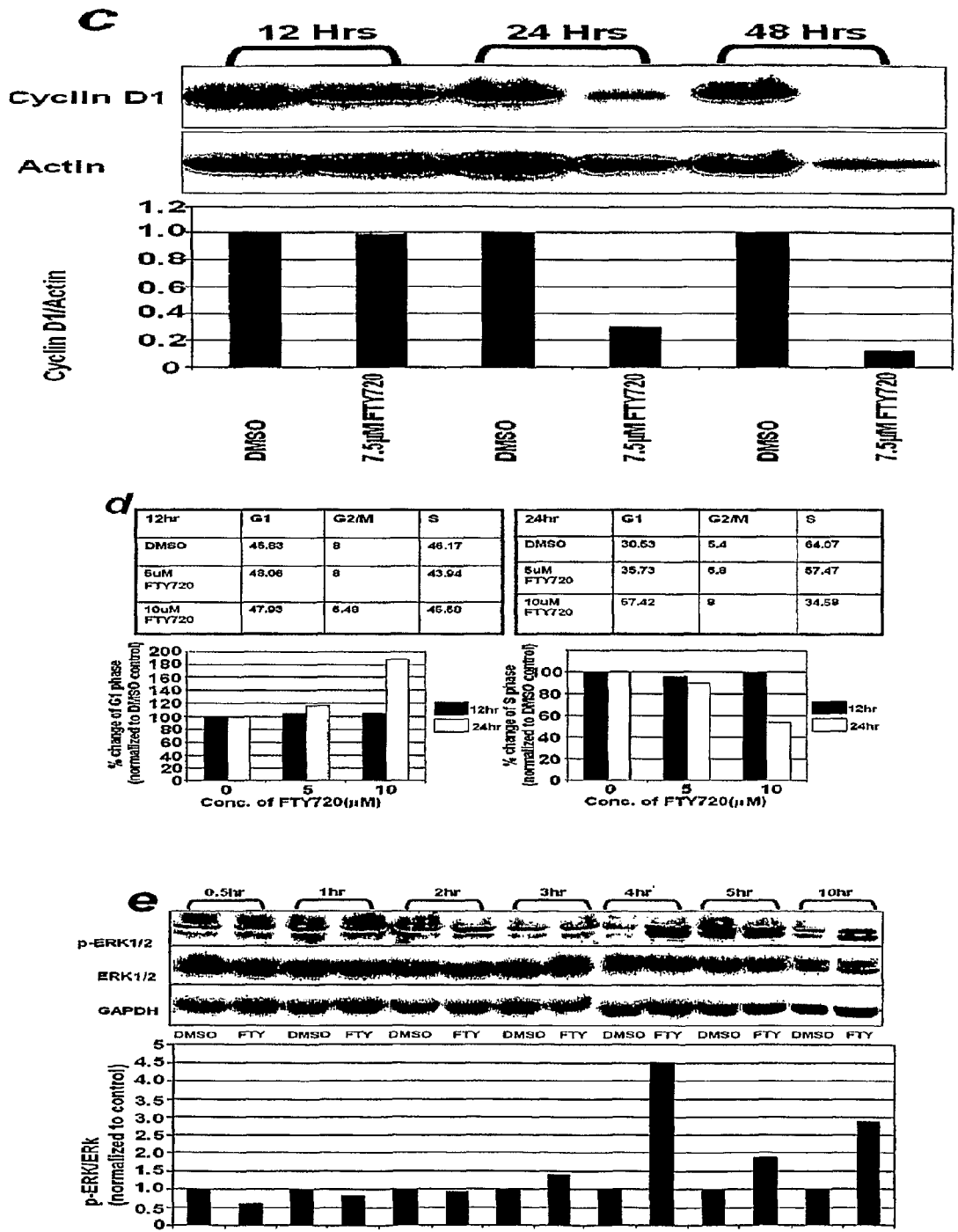
Figure 14 (c, d, e)

THERAPEUTIC AGENTS FOR THE TREATMENT OF LYMPHOID MALIGNANCIES

CROSS REFERENCE TO RELATED APPLICATIONS

This application is a national phase application of, claims priority to, and any other benefit of, International Application No.: PCT/US2007/012921, filed on Jun. 1, 2007, and entitled THERAPEUTIC AGENTS FOR THE TREATMENT OF LYMPHOID MALIGNANCIES, which claims priority to, and any other benefit of U.S. Provisional Application No. 60/803,845, filed on Jun. 2, 2006, both of which are hereby incorporated by reference in their entirety.

BACKGROUND

Despite the progress that has been made in the treatment of lymphoid malignancies, such as acute lymphoblastic leukemia (ALL) and chronic lymphocytic leukemia (CLL), the majority of patients with each of these diseases eventually develop resistance and ultimately die from their leukemia. In ALL and CLL, mechanisms of resistance have been shown to involve alternation in Bcl-2 family member expression that prevents apoptosis and aberrant signaling through the PKC, PI3 kinase/AKT, and ERK pathways in part mediated through stromal cell interactions. New therapies that act through novel mechanisms of action that either act independent of Bcl-2 family member expression and/or antagonize aberrant signal transduction pathways are therefore needed for both CLL and ALL. Normal lymphocytes utilize serine/threonine phosphatases such as PP1, PP2A, and PP2B to both inactivate signal transduction pathways and antagonize the action of Bcl-2 family members including Bcl-2 and Bad. In B-cell lymphoproliferative disorders, these same phosphatases are often silenced, a process that may contribute further to the drug resistance observed in these diseases. Therapeutic agents that activate serinine/threonine phosphatases such as PP2A have not been tested in the clinic for CLL and ALL.

FTY720 (2-Amino-2-[2-(4-octylphenyl) ethyl]propane 1,3-diol hydrochloride) is a synthetic compound produced by modification of a natural immunosuppressant, ISP-1. FTY720 was noted to interfere in T-cell trafficking and in pre-clinical studies was demonstrated to prolong survival of transplanted allograft organs without noticeable toxicity to the host. Early phase I/II clinical studies of FTY720 to treat and prevent organ rejection demonstrated promise. As a consequence, FTY720 is currently in Phase III clinical trials as immunosuppressant for renal transplant rejection. FTY720 elicits a lymphopenia resulting from a reversible redistribution of lymphocytes from circulation to secondary lymphoid tissues. FTY720 is phosphorylated by sphingosine kinase and the phosphorylated compound is a potent agonist at four sphingosine 1-phosphate receptors which modulate chemotactic responses and lymphocyte trafficking. FTY720 has been shown to bind to the sphingosine-1-phosphate (S1P) receptor, resulting in decreased number of circulating mature lymphocytes by acceleration of lymphocyte homing. Previous studies have also suggested that FTY720 might also promote activation of the serine/threonine phosphatase PP2A.

BRIEF DESCRIPTION OF FIGURES

FIG. 11: FTY720 does not cause cell cycle arrest in AML cell lines. Cell suspensions were treated with vehicle control, 1 uM, and 10 uM FTY720 for 48 hours. After fixation in ethanol, samples were stained with propidium iodide, and assessed for DNA content. Percentage of cells in subG1, G1, S, and G2-M for each cell line are depicted (FIG. 11A) with representative plots below for MV411 (FIG. 11B). Although cell cycle arrest is not seen, induction of apoptosis is noted by the increased fraction of sub G1 with FTY720 treatment.

FIG. 14: Mechanisms of FTY720 induced cell death in Primary MCL cells and MCL cell lines. 14a: FTY720 induced down modulation of Cyclin D1 in primary MCL cells. Primary MCL cells ($2\times106$/ml) were treated with 15 μM FTY720. Cell lysates were collected at 8 and 24 hrs post treatment and subjected to Western blotting using indicated antibodies. 14b: FTY720 induced down-modulation of phospho Akt and Akt prtotein levels in MCL cells. Mino cells ($5\times105$/ml) were treated with 15 μM FTY720. Cell lysates were collected at 8 and 24 hrs post treatment and subjected to Western blotting using indicated antibodies. 14c: FTY720 induced decrease in cyclin D1 in Mino cell line. Mino cells ($2\times106$/ml) were treated with 15 μM FTY720. Cell lysates were collected at 12, 24 and 48 hrs post treatment and subjected to Western Blotting using anti-Cyclin D1 antibody. The actin control shows comparable loading in each of the lanes. 14d: FTY720 induced cell cycle arrest in MCL cells. Mino cells ($5\times105$/ml) were treated with vehicle DMSO, 7.5 μM or 10 μM FTY720 for 12, 24 hrs. Cells were collected and fixed with ethanol and subsequently stained with propidium iodide. Cell cycle was analysed by flow cytometry. Results shown are representative of 3 independent experiments. 14e: FTY720 induced ERK1/2 phosphorylation in Mino cell line. Mino cells ($5\times105$/ml) were treated with 12 μM FTY720 for indicated time periods and cell lysates were collected at 8 and 24 hrs post treatment and subjected to Western Blotting using indicated antibodies.

DESCRIPTION

Figure 1:
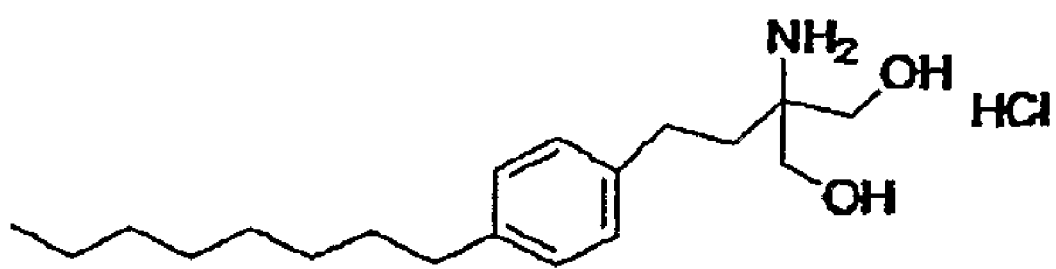
FIG. 1: Schematic diagram of the FTY720.

The present invention provides a novel method and composition for treating lymphoid malignancies, including, but not limited to, acute lymphoblastic leukemia (ALL), chronic lymphocytic leukemia (CLL), B-cell lymphoma, acute myeloid leukemia (AML), and mantle cell lymphoma (MCL). In some embodiments the patients are refractory to other treatments.

All publications, patent applications, patents, internet web pages and other references mentioned herein are expressly incorporated by reference in their entirety. When the definitions of terms in incorporated references appear to differ from the definitions provided in the present teachings, the definitions provided in the present teachings shall control.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

The term "refractory" represents previously treated patients which were either non responsive to treatment with the agent or had a response to treatment and then relapsed.

The term "treatment" as used herein includes partial or total destruction of the lymphoid malignancies with minimal destructive effects on normal cells.

The term "prevention" includes either preventing the onset of a clinically evident lymphoid malignancy altogether or preventing the onset of a preclinically evident stage of lymphoid malignancy in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence, while avoiding adverse side effects typically associated with alternative therapies.

The term "subject" for purposes of treatment includes any human or animal subject who has a disorder characterized by lymphoid malignancies or is at risk of developing such a disorder. Such disorders include, but are not limited to acute lymphoblastic leukemia (ALL), chronic lymphocytic leukemia (CLL), B-cell lymphoma, Acute Myeloid leukemia (AML), and mantle cell lymphoma (LCM). For methods described herein, the subject is any human or animal subject, and in some embodiments, the subject is a human subject who has developed or is at risk of developing a lymphoid malignancy. The subject may be at risk due to exposure to carcinogenic agents, being genetically predisposed lymphoid malignancies, and so on. Besides being useful for human treatment, the compounds of the present invention are also useful for veterinary treatment of mammals, including companion animals and farm animals, such as, but not limited to dogs, cats, horses, cows, sheep, and pigs.

The methods described herein may trigger cell death by a number of different mechanisms, however, an aspect of these methods is that they are able to induce apoptosis in lymphoid malignancies. The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are quietly removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. The methods described herein have been found to induce apoptosis even in lymphoid malignancies which, because of mutations, are otherwise resistant to apoptosis. Apoptosis can be distinguished from other treatment mechanisms by methods such as microscopy, which are known in the art.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other abnormal, rapidly dividing cells in a subject.

Derivatives are intended to encompass any compounds which are structurally related to the compounds of formula I which possess the substantially equivalent activity, as measured by the derivative's ability to induce apoptosis in lymphoid malignancies without substantial COX-2 inhibition. By way of example, such compounds may include, but are not limited to, prodrugs thereof. Such compounds can be formed in vivo, such as by metabolic mechanisms.

Also described herein are therapeutic methods of inducing apoptosis in lymphoid malignancies. The methods comprise administering a therapeutically effective amount of a compound of formula I to a subject having a disorder or being predisposed to a disorder involving lymphoid malignancies.

Also included in the family of compounds of formula I are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formula I may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, galactaric, and galacturonic acids. Suitable pharmaceutically acceptable base addition salts of compounds of formula I include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of formula I. All of these salts may be prepared by conventional means from the corresponding compounds of formula I by reacting, for example, the appropriate acid or base with the compound of formula I.

The present invention further embodies a pharmaceutical composition for inducing apoptosis in lymphoid malignancies, such as for treating, preventing, or delaying the onset of a lymphoid malignancy in a subject in need of such treatment. The pharmaceutical composition comprises a therapeutically effective amount of a compound of formula I or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, in the form of a pharmaceutical composition adapted to such a route, and in a dose effective for the treatment intended. The active compounds and composition may, for example, be administered orally, intra-vascularly, intraperitoneally, intranasally, intrabronchially, subcutaneously, intramuscularly or topically (including aerosol). With some subjects local administration, rather than system administration, may be more appropriate. Formulation in a lipid vehicle may be used to enhance bioavailability.

The methods described herein may be for either prevention or treatment purposes. The methods and compositions used herein may be used alone or in conjunction with additional therapies known to those skilled in the art in the prevention or treatment of disorders characterized by lymphoid malignancies. Alternatively, the methods and compositions described herein may be used as adjunct therapy. By way of example, the methods described herein may be used alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors including batiastat, marimastat, Agouron Pharmaceuticals AG-3340 and Roche RO-32-3555, or □vβ3 inhibitors may be used. Suitable agents which may be used in combination therapy will be recognized by those of skill in the art. Similarly, when combination therapy is desired, radioprotective agents known to those of skill in the art may also be used.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. In some embodiments, the pharmaceutical composition is made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is, in some embodiments, isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which, in some embodiments, is isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg in some embodiments, in the range of about 0.5 to 500 mg in other embodiments, and between about 1 and 200 mg in still other embodiments. In some embodiments, a daily dose of about 0.01 to 100 mg/kg body weight is appropriate. In other embodiments, a daily dose of between about 0.1 and about 50 mg/kg body weight, may be appropriate. The daily dose can be administered in single or multiple doses per day.

The following Examples are provided to illustrate various embodiments of the present invention and shall not be considered as limiting in scope.

EXAMPLE 1

FTY720 is an immunosuppressive agent that is being developed for preventing organ transplant rejection. Here we demonstrate here a novel mechanism by which FTY720 mediates cytotoxic effects in cell lines representing different B cell malignancies and in primary chronic lymphocytic leukemia (CLL) cells. FTY720 induced cellular apoptosis as detected by annexin V/propidium iodide staining in B cell lines representing acute lymphoblastic leukemia (ALL) and CLL patient derived primary $CD19^+$ B cells in a time and dose dependent manner. In-contrast to previous reports in T cell lines, FTY720 induced cytotoxicity in primary CLL cells and Raji cell line is independent of activation of caspase 3, 8 and 9 or poly-ADP ribose polymerase cleavage. Further, pan-caspase inhibitor Z-VAD-fmk rescued the cells from fludarabine but not FTY720 induced apoptosis. Over-expression of Bcl-2 failed to protect transformed B-cells from FTY720 induced apoptosis suggesting Bcl-2 independent cytotoxic effect. Interestingly, FTY720 induced consistent increase in protein phosphatase 2A (PP2A) activity and concentrations of okadaic acid that inhibited the FTY720 induced PP2A activity also resulted in inhibition of FTY720 mediated cytotoxicity in primary CLL cells and B cell lines, indicating a role for PP2A activation in FTY720 mediated cytotoxicity. Further, FTY720 treatment resulted in prolonged survival associated with significant in-vivo therapeutic efficacy in a xenograft SCID mouse model of dissemeninated B cell lymphoma/leukemia. These results provide the first evidence for a PP2A-dependent and caspase-independent cytotoxicity of FTY720 in B cells and the effectiveness of FTY720 as a therapeutic agent in a variety of B-cell malignancies including CLL.

Materials and Methods

Cells: Blood was obtained from patients with B-cell CLL with informed consent under a protocol approved by the hospital internal review board. All patients examined in this series had immunophenotypically defined CLL as outlined by the modified 96 National Cancer Institute criteria. B-CLL cells were isolated from freshly donated blood using ficoll density gradient centrifugation (Ficoll-Paque Plus, Amersham Biosciences, Piscataway, N.J.). Isolated mononuclear cells were incubated in RPMI 1640 media (Gibco/Invitrogen, Carlsbad, Calif.) supplemented with 10% heat-inactivated fetal bovine serum (FBS, Hyclone Laboratories, Logan, Utah), 2 mM L-glutamine (Invitrogen, Carlsbad, Calif.), and penicillin (100 U/mL)/streptomycin (100 µg/ml) [Sigma-Aldrich, St. Louis] at 37° C. in an atmosphere of 5% $CO_2$. Freshly isolated B-CLL cells were used in all experiments described herein. Enriched B-lymphocyte fractions were prepared by using MACS negative selection kit by Miltenyi Biotech (Auburn, Calif.) or by "Rosette-Sep" kit from Stem Cell Technologies (Vancouver, British Columbia, Canada) according to the manufacturer's instructions. Human B-lymphocyte cell lines Raji and Ramos were obtained from ATCC (Manassas, Va.) and the MEC cells were obtained from German cell line bank (Braunschweig, Germany). The 697-neo and 697-Bcl-2 cell lines were kind gift from Dr. John Reed (Burnham Institute, La Jolla, Calif.). Cells were cultured at 37° C. in an atmosphere of 5% $CO_2$ in RPMI 1640 media (Gibco/Invitrogen, Carlsbad, Calif.) supplemented with 10% fetal bovine serum (Gibco/Invitrogen).

Chemical Reagents: FTY720 was synthesized according to a reported procedure (32), and its identity and purity were confirmed by nuclear magnetic resonance and mass spectrometry. Z-VAD-fmk (Sigma-Aldrich, St. Louis) and Okadaic acid (Upstate Biotechnology, Inc., Lake Pacid, N.Y.) were used at indicated concentrations.

Analysis of cell viability and apoptosis: The cell viability was carried out by dual staining with Annexin V conjugated to flourescein-isothyocyanate (FITC) and Propidium iodide (PI) as described previously. Briefly, $1 \times 10^6$ cells were stained with Annexin V-FITC (BD Pharmingen) and Propidium iodide (BD Pharmingen) for 15 minutes in dark and analyzed by flow cytometry using a Beckman-Coulter EPICS XL cytometer (Beckman-Coulter, Miami, Fla.). Apoptotic cells were identified as Annexin V and/or PI positive cells. Cells excluding both FITC and PI were considered to be viable. The Annexin $V^-/PI^-$ cells are represented as % live cells normalized to untreated controls.

MTT assay: Cell growth was assessed using the MTT assay. The cells ($1 \times 10^6$) were placed in 200 µl of media±indicated concentrations of FTY720 in each well of a 96 well flat bottomed microtitre plates in triplicate cultures and incubated overnight at 37° C. in an incubator at 5% $CO_2$ atmosphere. MTT was prepared at 5 mg/ml in PBS and added to each well at 12 or 36 hours. The cell cultures were continued for another 12 hrs at 37° C. The color development solution was added to each well and the absorbance was measured using a micro culture plate reader with a wave length of 570 nm. The cell viability was expressed as percentage of absorbance in cells with indicated treatments to that in cells with vehicle control treatment.

Western blotting. Immunoblot assays were performed as described previously.(34) Cell lysates were prepared and quantified by the bicin choninic acid (BCA) method (Pierce, Rockford, Ill.). Lysates with 50 µg of total protein were separated using 10% sodium dodecyl sulfate-polyacrylamide-gel electrophoresis, and transferred to 0.2 µm nitrocellulose membranes (Schleicher & Schuell, Keene, N.H.). The blots were probed with indicated primary antibodies followed by Horseradish peroxidase (HRP)-conjugated goat anti-rabbit IgG or goat anti-mouse IgG (Bio-Rad Laboratories, Richmond, Calif.). Detection was made with chemiluminescent substrate (SuperSignal, Pierce Inc. Rockford, Ill.). The PARP (Ab-2) and Caspase 9 antibodies were purchased from Oncogene/Calbiochem/EMD Biosciences (San Diego, Calif.). The Caspase 3 (AR-14 caspase 3/cpp32 and caspase 8 (AR-18) antibodies were kind gift from Dr. John Reed (Burnham Institute, La Jolla, Calif.).

PP2A Activity: The protein phosphatase activity of total cellular lysate was determined by measuring the generation of free $PO_4$ from the threonine phosphopeptide using the malachite green-phosphate complex assay as described by the manufacturer (Upstate, Charlottesville, Calif.). Cell lysates were prepared in a low detergent lysis buffer (1% Nonidet P-40, 10 mM HEPES, 0.5M NaCl, 10% Glycerol, 1 mM PMSF, 5 mM Benzamidine, 10 µg/ml leupeptin). The phosphatase assay was performed in a PP2A-specific reaction buffer (Upstate) using 750 µM phosphopeptide substrate. After 30-min incubation at 30° C. malachite dye was added, and free phosphate was measured by optical density at 650 nM. To avoid variability among different immunoprecipitated samples, the phosphatase activities were normalized with the amount of PP2A immunoprecipitated, as detected and quantified by western blot analysis of each treatment group.

In vivo therapeutic efficacy evaluation in a xenograft model: The in-vivo evaluation of FTY720 was carried out using the disseminated lymphoma bearing SCID mouse xenograft model. This model was generated using human Raji B cell line injected into SCID mice as previously described. Raji cells were cultured in RPMI1640+10% FBS. Confluent cultures with >95% viability were confirmed to express human CD19 by flow cytometry. Twenty six female 6-8 week-old C.B.-17 SCID mice (Taconic Farm, Germantown, N.Y.) were injected with $2 \times 10^6$ cells intravenously (i.v) in 200 ul sterile PBS via the tail vein. Seventy two hours post inoculation, the animals were divided into 4 equal treatment groups. The first 3 groups served as control and received vehicle, trastuzumab or rituximab injection; and the 4th group consisted of animals treated with FTY720 (5 mg/kg) every day for 2 weeks i.p. The FTY720 untreated SCID mice inoculated with Raji cells developed symptomatic central nervous system involvement resulting in progressive hind limb paralysis associated with decreased mobility, loss of body weight and death 17-21 days post-inoculation. All the animals were monitored daily for signs of illness and sacrificed immediately if hind limb paralysis, respiratory distress or 30% body weight loss was noted. Body weight was measured once every week. The end-point of the study was survival defined as the time for the development of hind limb paralysis. Animals that reached the end-point or survived after 6 months of observation were sacrificed by cervical dislocation. Histopathological examination of liver, lung and brain was performed to detect any residual disease. The presences of the $CD19^+$ cells were evaluated in the bone marrow of these mice by flow cytometry.

Statistical analysis of data. All the analysis was performed by statisticians in the Center for Biostatistics, the Ohio State University. SPSS software (version 9.0, SPSS, Chicago, Ill.) was used for all the statistical analysis. Significance was tested based on 2-sided P values. Comparison was made between different groups using Wilcoxon signed rank test and paired t-test for in vitro studies. Log-rank test was applied for analysis of animal survival study.

Figure 2:
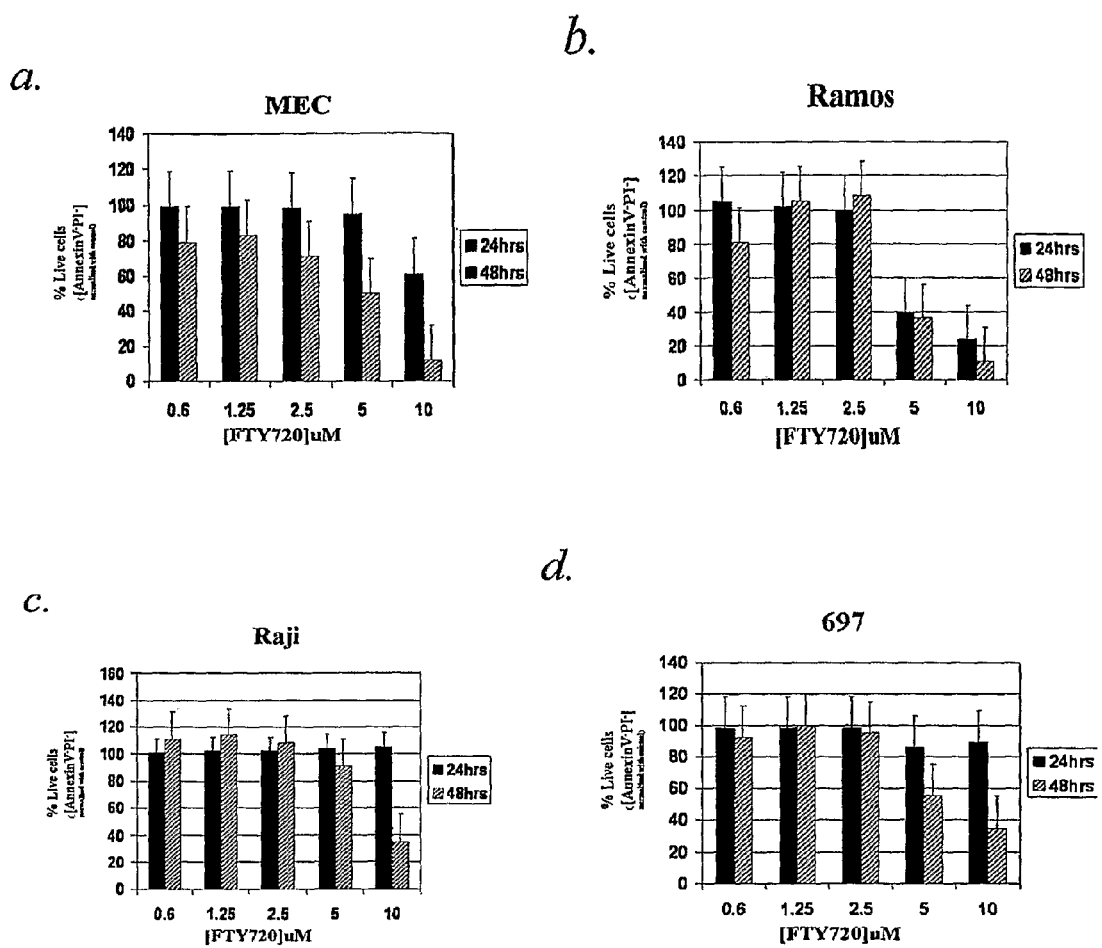
FIG. 2: FTY720 mediated cytotoxicity in MEC, Ramos, Raji and 697 B cell lines—Dose and time kinetic analysis. MEC (panel a), Ramos (panel b), Raji (Panel c) or 697 (Panel d) cells ($1\times10^5$ cells/ml) were incubated in the presence of indicated concentrations of FTY720 or DMSO vehicle for 24 hours (filled bar) or 48 hours (Hatched bar). The cells were stained with Annexin-V-FITC and propidium iodide as described in the section on "Materials and methods". The cells were analyzed by flow cytometry and data collected under list mode. The data shown represent % Annexin-$V^-$/$PI^-$ viable cells±SD that are normalized to media control. (n=3; *p<0.001) when compared to media control).

FTY720 mediated cytotoxicity in B cell lines and purified B cells from CLL patients. Several studies have demonstrated a role for FTY720 in regulation of T cell homing in-vivo and cytotoxicity in vitro in T cell lines. (25,v 27, 36) However systematic analysis of the effect of FTY720 in acute and chronic B-cell lymphoid leukemia has not been performed. We first synthesized FTY720 as outlined in the methods section. Incubation of MEC, a B cell line established from a CLL patient, Ramos and Raji cell lines representing Burkitt's leukemia/lymphoma or acute lymphoblastic leukemia cell lines 697 and RS4-11 with 0.6 uM, 1.25 uM, 2.5 uM, 5 uM or 10 uM of FTY720 resulted in dose dependent inhibition of viable cells with concomitant increase in Annexin $V^+$ and/or $PI^+$ cells as measured by flow cytometry (FIG. 2). The FTY720 mediated cytotoxicity in each of these cell lines was time dependent with maximal effect seen as late as 48 hours post treatment. The dose and time dependent effect of FTY720 induced decrease in viable cells was further reflected in parallel MTT assay (data not shown). Similar results were also obtained in RS11,4 cell line (data not shown).

Figure 3:
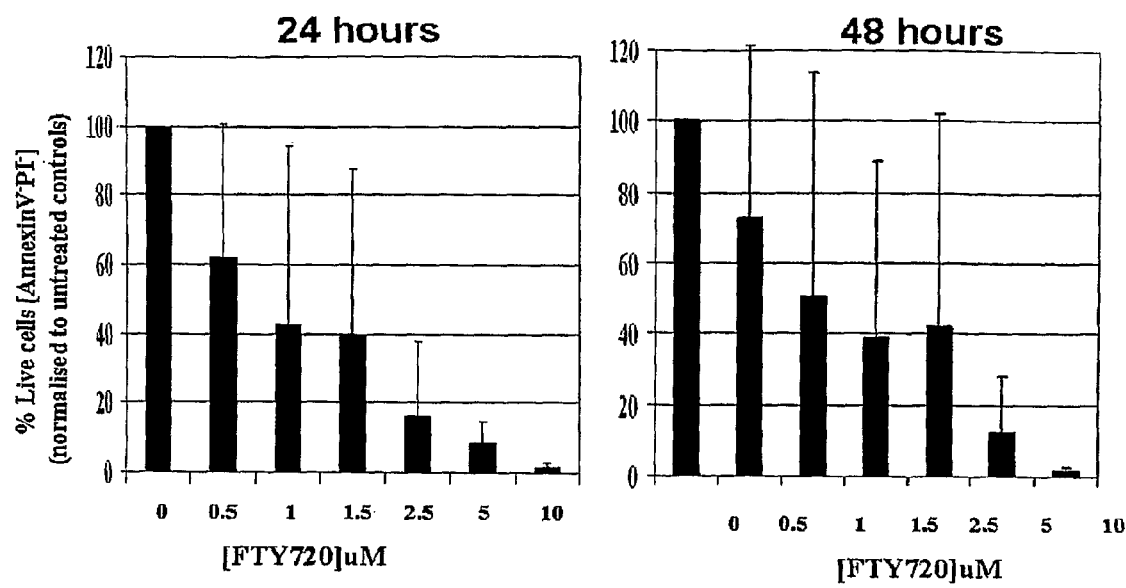
FIG. 3: FTY720 mediated cytotoxicity in CD19+ B cells from CLL patients—Dose and time kinetic analysis. Purified $CD19^+$B-lymphocytes from CLL patients ($1\times10^6$/ml media) were incubated with indicated concentrations of FTY720 or DMSO vehicle for 24 hours (left panel) or 48 hours (right panel). The cells were stained with Annexin-V-FITC and propidium iodide as described in the section on "Materials and methods". The cells were analyzed by flow cytometry and data collected under list mode. The data shown represent % Annexin-$V^-$/$PI^-$ viable cells±SD that are normalized to media control (n=15) *p<0.001 when compared to untreated vehicle control)

B-CLL cells are reported to be resistant to apoptosis in-vivo. To systematically analyze the effects of FTY720 on B-CLL cells, purified $CD19^+$ cells from B-CLL patients were incubated with increasing concentrations of FTY720 ranging from 0, 0.5, 1, 1.5, 2.5, 5 or 10 uM. The cytotoxic effects were independently determined by flow cytometry using propidium iodide (PI) and Annexin V conjugated FITC reagents. Populations excluding both PI and Annexin V-FITC staining were considered viable. Cells that were Annexin $V^+/PI^-$, Annexin $V^+/PI^+$ or $V^-/PI^+$ were considered to be apoptotic. Incubation of CLL B cells with FTY720 resulted in dose and time dependent decrease in viability of $CD19^+$ B cells from 15 CLL patients. (p<0.0001 when compared to untreated and 10 uM-treated groups). The effect of FTY720 was time dependent as a consistent significant reduction in viability was observed as early as 24 hrs in dose dependent manner indicating potential early cytotoxic mechanisms (FIG. 3). Consistent with increased cell death the FTY720 treated cells also exhibited decreased viability as evidenced by MTT assays (data not shown).

Figure 4:
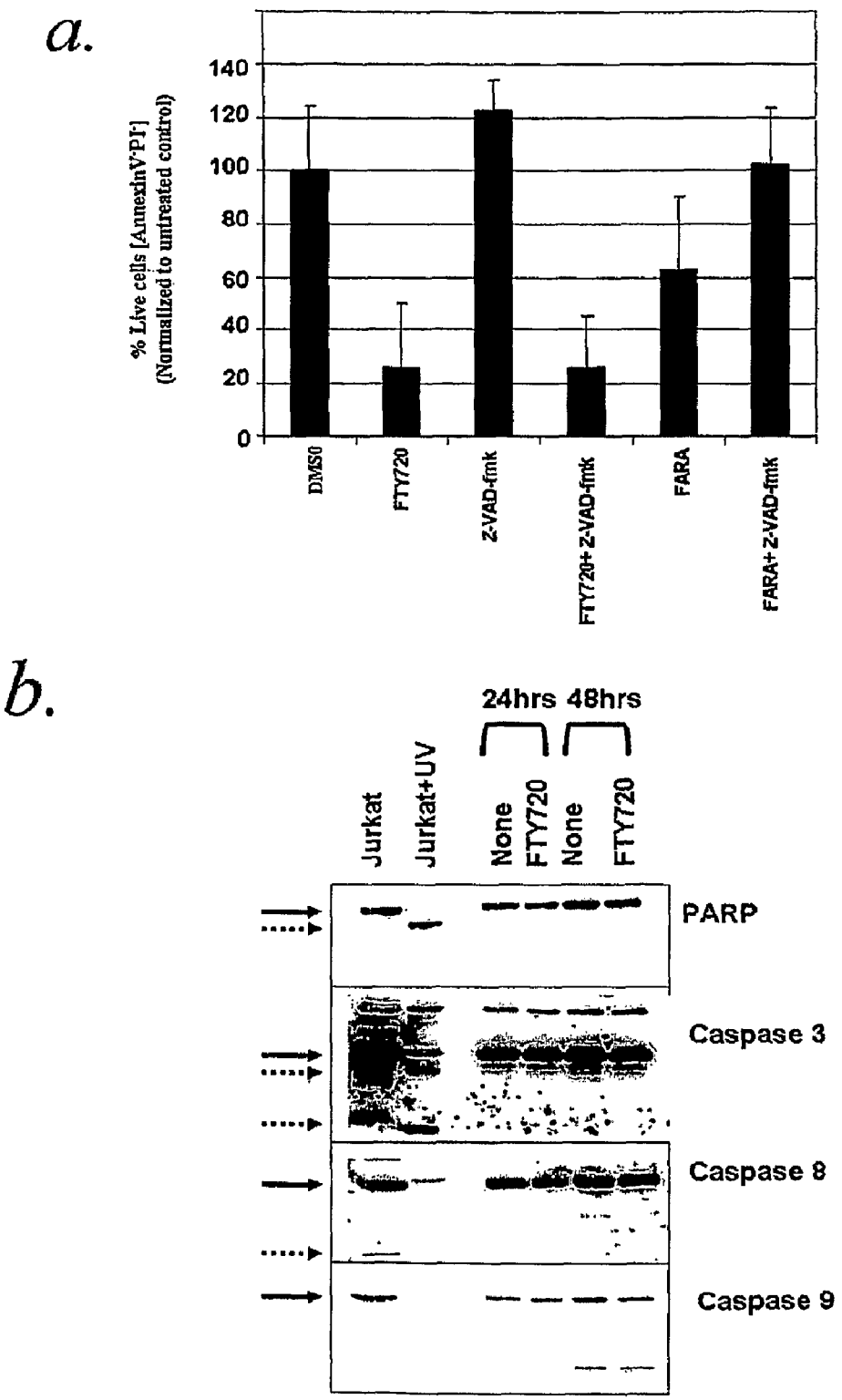
FIG. 4. FTY720 induced cytotoxicity in CLL cells is independent of caspase activation. Panel 4a: Purified B-lymphocytes from CLL patients ($1\times10^6$/ml media) were incubated with 10 uM FTY720 in the presence or absence of z-VAD-fmk (150 uM) for 24 hours. The cells were stained with Annexin-V-FITC and propidium iodide as described in the section on "Materials and methods". The cells were analyzed by flow cytometry and data collected under list mode. The data shown represent % Annexin-$V^-$/$PI^-$ viable cells±SD that are normalized to media control. (n=3;*p=0.001 when compared to FARA treated group; **p=0.998 when compared to FTY720 treated group). Panel 4b: Purified B-lymphocytes from CLL patients ($1\times10^6$/ml media) were incubated with DMSO (None) or 10 uM FTY720 for 24 and 48 hrs. Western blot analysis of the lysates from each of the conditions were assessed for cleaved and uncleaved PARP, Caspase 3, caspase 8 and caspase 9 as described in the section on "Materials and methods". The bold arrow indicates the uncleaved form of each of the proteins and the broken arrows indicate cleaved products. Untreated and UV treated Jurkat cell lysates were used as positive controls.

FTY720 induced apoptosis in CLL cells is not dependent on activation of caspases, the cysteine proteases of CED3/ICE family Several therapeutic agents such as glucocorticoids and chemotherapeutic agents such as fludarabine, chlorambucil and 2-chloro-2-deoxyadenosine induce cellular cytotoxicity in CLL cells through activation of caspases, the cysteine proteases of CED3/ICE family. Inhibition of these caspases results in abrogation of apoptosis mediated by the cytotoxic stimuli. To determine if caspase activation is involved in FTY720 induced cell death in primary CLL cells, we pretreated $CD19^+$ CLL cells prior to treatment with FTY720 with a broad spectrum caspase inhibitor z-VAD-fmk. As shown in FIG. 4a, concentrations of z-VAD-fmk (150 uM) that effectively rescued fludarabine induced apoptosis, failed to prevent FTY720 induced apoptosis [n=5; p=0.001-fludarabine versus fludarabine plus Z-VAD-fmk; p=0.99–FTY720 vs FTY720+Z-VAD-fmk). Activation of caspases results in cleavage of key cellular proteins including poly-ADP-ribose polymerase (PARP) and Caspase 3, 8 and 9. Consistent with the inability of z-VAD-fmk to rescue FTY720 induced apoptosis, Western blot analysis of lysates prepared from $CD19^+$ B cells from CLL patients at 24 and 48 hours post treatment with FTY720 failed to reveal PARP cleavage (FIG. 4b). In addition caspases 3, 8 and 9 also remained in precursor forms demonstrating absence of caspases activation in FTY720 treated cells. Similar to the CLL cells, FTY720 induced cytotoxicity in Raji B cell line was not accompanied by activation of caspase 3, 8 or 9 or rescued by z-VAD-fmk (data not shown).

Figure 5:
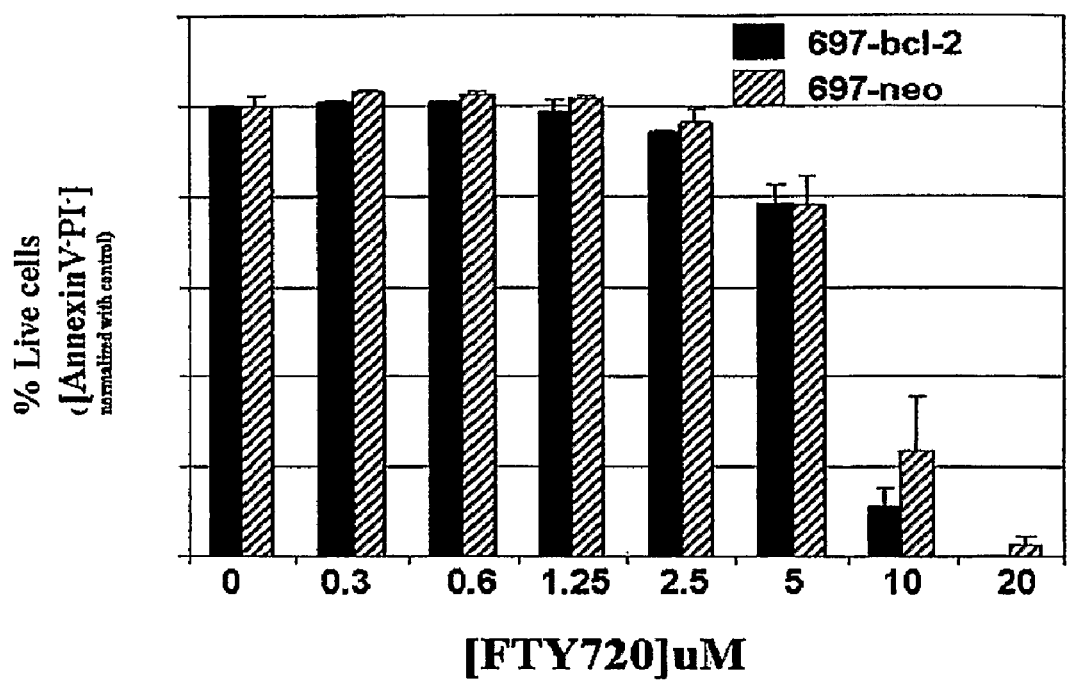
FIG. 5. FTY720 induced cytotoxicity in B cells is Bcl-2 independent. 697-neo empty vector (hatched bar) or 697-bcl-2 (Filled bar) transfected 697 cells ($1\times10^5$ cells/ml) were incubated in the presence of indicated concentrations of FTY720 or DMSO vehicle for 24 hours. The cells were stained with Annexin-V-FITC and propidium iodide as described in the section on "Materials and methods". The cells were analyzed by flow cytometry and data collected under list mode. The data shown represent % Annexin-$V^-$/$PI^-$ viable cells±SD that are normalized to media control.

FTY720 induced apoptosis is Bcl-2 independent The proto-oncogene Bcl-2 is over expressed in CLL B cells. The resistance to apoptosis has been implicated to the high levels of Bcl-2 expression in these cells. Decreased cell viability during in-vitro culture conditions or in response to treatment with cytotoxic agents correlates with down regulation of bcl-2 expression. Further, constitutive over expression of Bcl-2 in cell lines results in resistance to apoptosis. In order to determine if sustained expression of Bcl-2 will result in protection from FTY720 induced apoptosis, 697 cells stably transfected with neomycin carrying vector or Bcl-2 expression vector were tested with increasing concentrations of FTY720 at 24, 48 and 72 hours. As shown in FIG. 5, FTY720 induced comparable levels of cellular cytotoxicity in both the control 697-neo cell line and the 697-Bcl-2 over expressing cell line at 24 hours (FIG. 5). Similar effects of FT720 was also observed in extended cultures at 48 and 72 hrs tested (data not shown) Further, Western blot analysis of protein extract in the Bcl-2 high expressing cells were not altered in response to FTY720 treatment indicating the FTY720 mediated cellular cytotoxicity is independent of the levels of Bcl-2 expression (data not shown).

Figure 6:
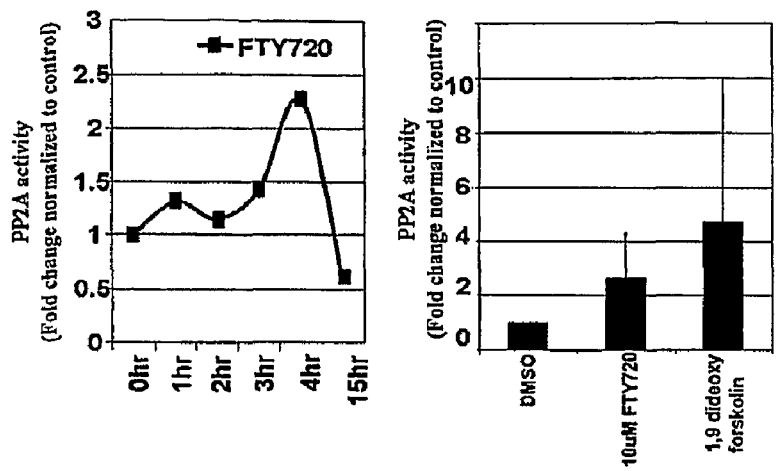
FIG. 6. FTY720 induced cytotoxicity in CLL cells is dependent on activation of PP2A. Panel a: FTY720 induced PP2A activity in CD19+ B cells from CLL patients: Purified B-lymphocytes from CLL patients ($1\times10^6$/ml media) were incubated with DMSO or 10 uM FTY720 for 0, 1, 2, 3, or 15 hours. The PP2A activity in the cell lysates were measured as described in the section on "Materials and methods". The left panel shows the time kinetics of a representative experiment. The right panel shows summary of PP2A activity at 4 hours in 5 independent samples in response to DMSO, 10 uM FTY720 or 1,9, dideoxy forskolin. Panel b: FTY720 induced PP2A activity in CD19+ B cells is inhibited by Okadaic acid. Purified B-lymphocytes from CLL patients ($1\times10^6$/ml media) were pretreated with media or okadaic acid (5 nM) for 2 hours followed by incubation with DMSO or 10 μM FTY72 for indicated time periods. The PP2A activity in the cell lysates were measured as described in the section on "Materials and methods". (n=4. *p<0.001 when compared to FTY720 treated group). Panel c: FTY720 induced cellular cytotoxicity is partially rescued by okadaic acid. Purified B-lymphocytes from CLL patients ($1\times10^6$/ml media) were pretreated with media or okadaic acid (5 nM) for 2 hours followed by incubation with DMSO or 10 uM FTY720. The cells were stained with Annexin-V-FITC and propidium iodide as described in the section on "Materials and methods". The cells were analyzed by flow cytometry and data collected under list mode. The data shown represent % Annexin-V$^-$/PI$^-$ viable cells±SD that are normalized to media control. (n=4; *p=0.06 when compared to FTY720 treated group).
Figure 6:
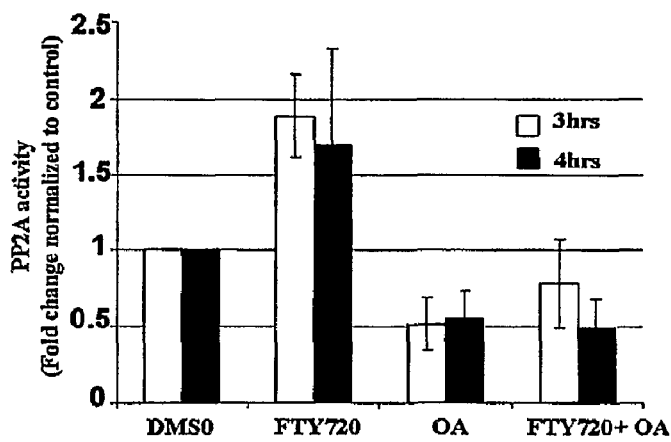
Figure 6:
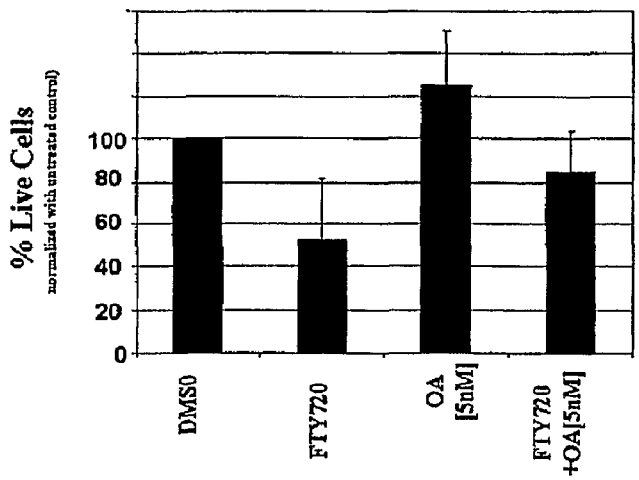
Figure 7:
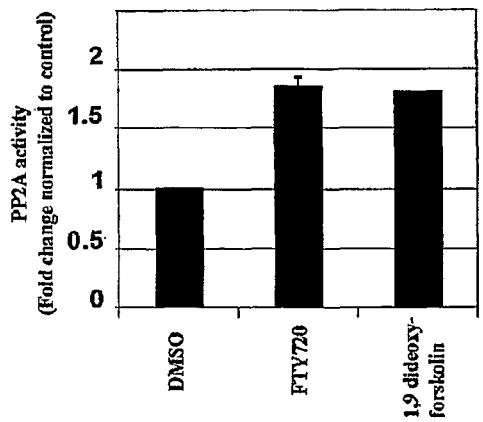
FIG. 7. FTY720 induced cytotoxicity in Ramos B cell line is dependent on activation of PP2A. Panel a: FTY720 induced PP2A activity in Ramos B cell line. Ramos B cells ($1\times10^5$/ml media) were incubated with DMSO, 10 uM FTY720 or 10 uM 1,9 dideoxy forskolin for 4 hours. The PP2A activity in the cell lysates were measured as described in the section on "Materials and methods". The result shown is a representative of 2 independent experiments. Panel b: FTY720 induced PP2A activity in Ramos B cell line is inhibited by Okadaic acid. Ramos B cells ($1\times10^5$/ml media) were pretreated with media or indicated concentrations of okadaic acid for 2 hours followed by incubation with DMSO or 10 uM FTY72 for 4 hours. The PP2A activity in the cell lysates were measured as described in the section on "Materials and methods". The results shown is a representative of 2-3 independent experiments. Panel c: FTY720 induced cellular cytotoxicity is partially rescued by okadaic acid in Ramos B cells. Ramos B cells ($1\times10^5$/ml media) were pretreated with media or indicated concentrations of okadaic acid (5 nM) for 2 hours followed by incubation with DMSO or 10 uM FTY720. The cells were stained with Annexin-V-FITC and propidium iodide as described in the section on "Materials and methods". The cells were analyzed by flow cytometry and data collected under list mode. The data shown represent % Annexin-V$^-$/PI$^-$ viable cells±SD that are normalized to media control. The results shown is the mean±SD of 5 independent experiments.
Figure 7:
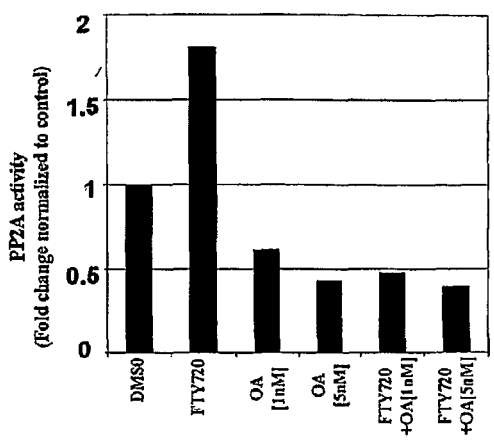
Figure 7:
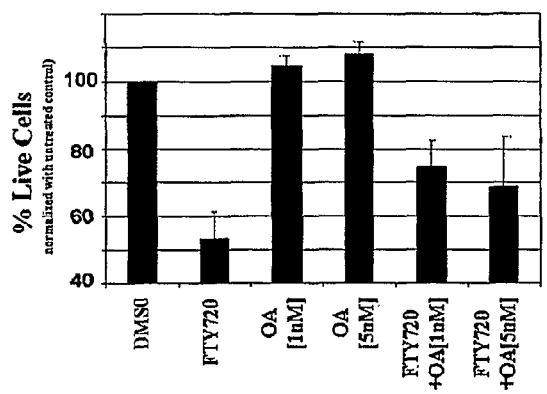

FTY720 mediated apoptosis is dependent on PP2A activation in CLL cells FTY720 has been shown to induce activation of PP2A in several cell lines including Jurkat T cells. In order to determine if FTY720 induced activation of PP2A enzyme in CD19+ B cells from CLL patients were treated with 10 uM FTY720 for 0, 1, 2, 3, 4 and 15 hrs and the PP2A activity in the lysates were quantified using a functional assay following immunoprecipitation of PP2A enzyme. As reported previously in other systems, FTY720 induced a consistent 2-3 fold increase in PP2A activation with the peak response observed at 4 hour post treatment (FIG. 6a). The FTY720 induced PP2A activity is associated with activation of PP2A enzyme as pretreatment of CLL cells with 5 nM okadaic acid, a concentration that has been shown to inhibit protein phosphatase activity in cells, resulted in inhibition of the FTY720 induced PP2A activation as much as 3 fold (FIG. 6b). Further, the FTY720-induced apoptosis is dependent on the PP2A activation as concentrations of okadaic acid that resulted in inhibition of FTY720-induced PP2A activation, also resulted in inhibition of FTY720 induced cellular cytotoxicity (FIG. 6c). Similar phenomenon was also observed in Ramos B cell line. FTY720 induced activation of PP2A in Ramos cell line as early as 3 hours and this induced PP2A activity was inhibited by okadaic acid (FIG. 7a-b). Pretreatment of Ramos cells with okadaic acid resulted in inhibition of FTY720 induced apoptosis indicating a role for FTY720 induced PP2A activation in cellular cytotoxicity (FIG. 7c).

Figure 8:
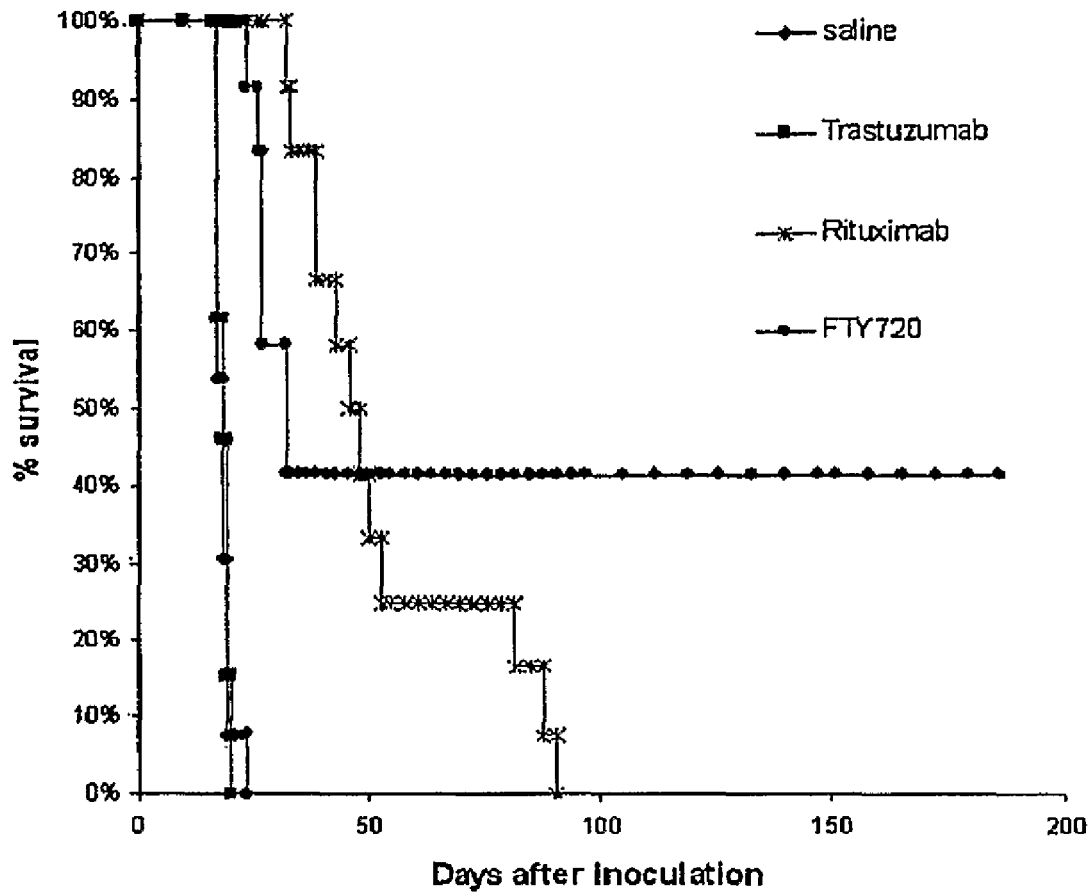
FIG. 8. In-vivo therapeutic evaluation of FTY720 in a SCID xenograft mouse model of disseminated lymphoma/leukemia. Twenty six female 6-8 week-old C.B.-17 SCID were injected with $2\times10^6$ Raji cells intravenously (i.v) by tail vein in 200 ul sterile PBS. Seventy four hours post inoculation, the animals were divided into 4 equal treatment groups. The first 3 groups served as control and received vehicle, trastuzumab or rituximab injection and the 4th group consisted of animals treated with FTY720 (5 mg/kg) every day for 2 weeks i.p. All the animals were monitored daily for signs of illness and sacrificed immediately if hind limb paralysis, respiratory distress or 30% body weight loss was noted. The end-point of the study was survival defined as the time for the development of hind limb paralysis. The median survival time for FTY720 treated mice was 47 days (95 % CI 39-53). This is significantly prolonged compared with placebo controls (18 days, 95% CI 17-19; FTY720 v.s. placebo P<0.0001).

In-vivo evaluation of FTY720 in a SCID xenograft mouse model of B cell malignancy In order to determine the in-vivo effect of FTY720 in preventing B cell tumor growth, we used the Raji cell-inoculated disseminated leukemia/lymphoma xenograft SCID mouse model. Intravenous injection of Raji cells in SCID mice resulted in infiltration of neoplastic cells in various organ systems including bone marrow, spleen, lymph nodes and central nervous system (CNS) as revealed by histological analysis of tissue sections. Flow cytometric analysis of bone marrow cells from these mice exhibited presence of human CD19+ and human CD20+ cells. Multifocal neoplastic cell infiltration in the meninges associated with hind leg paralysis between 17-21 days was noticed in all the control Raji cell injected mice analyzed. Reproducible and reliable engraftment of Raji cells, favored this model for investigating the in vivo therapeutic efficacy of FTY720, using hind limb paralysis time/survival time as primary endpoint for evaluation. The median survival time for FTY720 treated mice was 47 days (95% CI 39-53). This is significantly prolonged compared with placebo controls (18 days, 95% CI 17-19; FTY720 vs placebo P<0.0001). After a follow-up period of 200 days, 4 of the 12 mice treated with FTY720 were able to survive without signs of disease including loss of body weight, lethargy, ruffed coat or hind limb paralysis (FIG. 8).

The studies described in Example 1 demonstrate that FTY720 is a potent cytotoxic agent for lymphoid malignancies, including acute lymphoblastic leukemia, chronic lymphocytic leukemia and B-cell lymphoma. These studies are derived from a wide range of cell lines and primary tumor cells from patients with CLL. Importantly, our data demonstrate that FTY720 is different from many therapeutic agents currently under study in lymphoid malignancies. First, FTY720 mediates cellular cytotoxicity that is not dependent on activation of caspases cascade as demonstrated in both primary CLL cells and lymphoblastic cell lines. Second, FTY720 mediates its cytotoxic effect independent of Bcl-2 expression, a finding that is relatively uncommon among most therapeutics used to treat lymphoid malignancy. Finally, the biologic effect of FTY720 on ALL and CLL cells seems to be in part explained by activation of PP2A and potentially other phosphatases distinguishing it from other therapeutics currently used in these diseases. These in vitro data demonstrating a novel mechanism of action and potential promising therapeutic efficacy are further supported by in vivo data in a xenograft disseminated leukemia cell model where FTY720 significantly prolongs survival and cures a subset of mice. Considered together, our data provide strong support for the use of FTY720 for the treatment of B-cell ALL and CLL.

The ability of FTY720 to mediate caspase independent death in ALL and CLL cells is different than previously reported. Two separate studies examining both the Jurkat T lymphoblast cell line and multiple myeloma cell lines suggested caspase activation was important. While we found Raji and 697 lymphoblastic cell lines and primary CLL patient samples to be caspase independent as described herein, subsequent investigation of the Ramos cell line demonstrates caspase activation to be important to FTY720 mediated death. Overall, these data suggest that FTY720 treatment can mediate cellular apoptosis in caspase dependent and independent mechanisms depending on the cell type. The caspase independent cytotoxicity in these cells indicates alternate mechanisms of cytotoxicity by FTY720 in CLL cells.

FTY720 has been shown to mediate activation of PP2A enzyme in Jurkat T cells. Consistent with the previous reports, FTY720 induced time dependent activation of PP2A enzymatic activity in CLL and B cell lines. In addition, the FTY720 induced PP2A activity can be blocked by okadaic acid, an inhibitor of PP2A. Consistent with a role for FTY720 induced PP2A activation in induction of apoptosis, concentrations of okadaic acid that inhibited FTY720 induced PP2A activation also resulted in partial inhibition of FTY720 induced apoptosis. This suggests a role for activated PP2A or other phosphatases activated by this agent in FTY720 induced apoptosis of CLL and lymphoblast cells.

To this point, FTY720 has been solely developed as an immunosuppressive agent for the prevention of organ transplant rejection. Toxicity in the phase I, II, and III studies of FTY720 have been relatively unremarkable relative to dose limiting toxicities observed with many anti-cancer therapies. Our in vitro and in-vivo evaluation of FTY720 in acute and chronic lymphoid leukemia suggests that this agent may have potential therapeutic benefit in these diseases. It is quite possible that the therapeutic dose to activate PP2A and promote apoptosis will be different than the immunosuppressive dose used in the organ transplant studies performed to date. Our PP2A activity induction data occurring soon after treatment with FTY720 in primary CLL cells corresponding to the concentrations that apoptosis occurs provides a biomarker to accompany phase I dose escalation in this disease.

In conclusion, our in vitro and in vivo data demonstrate that FTY720 exhibits potent anti-growth and pro-apoptotic properties in lymphoid malagnancies, and good results have been observed in ALL and CLL cells.

EXAMPLE 2

Figure 9:
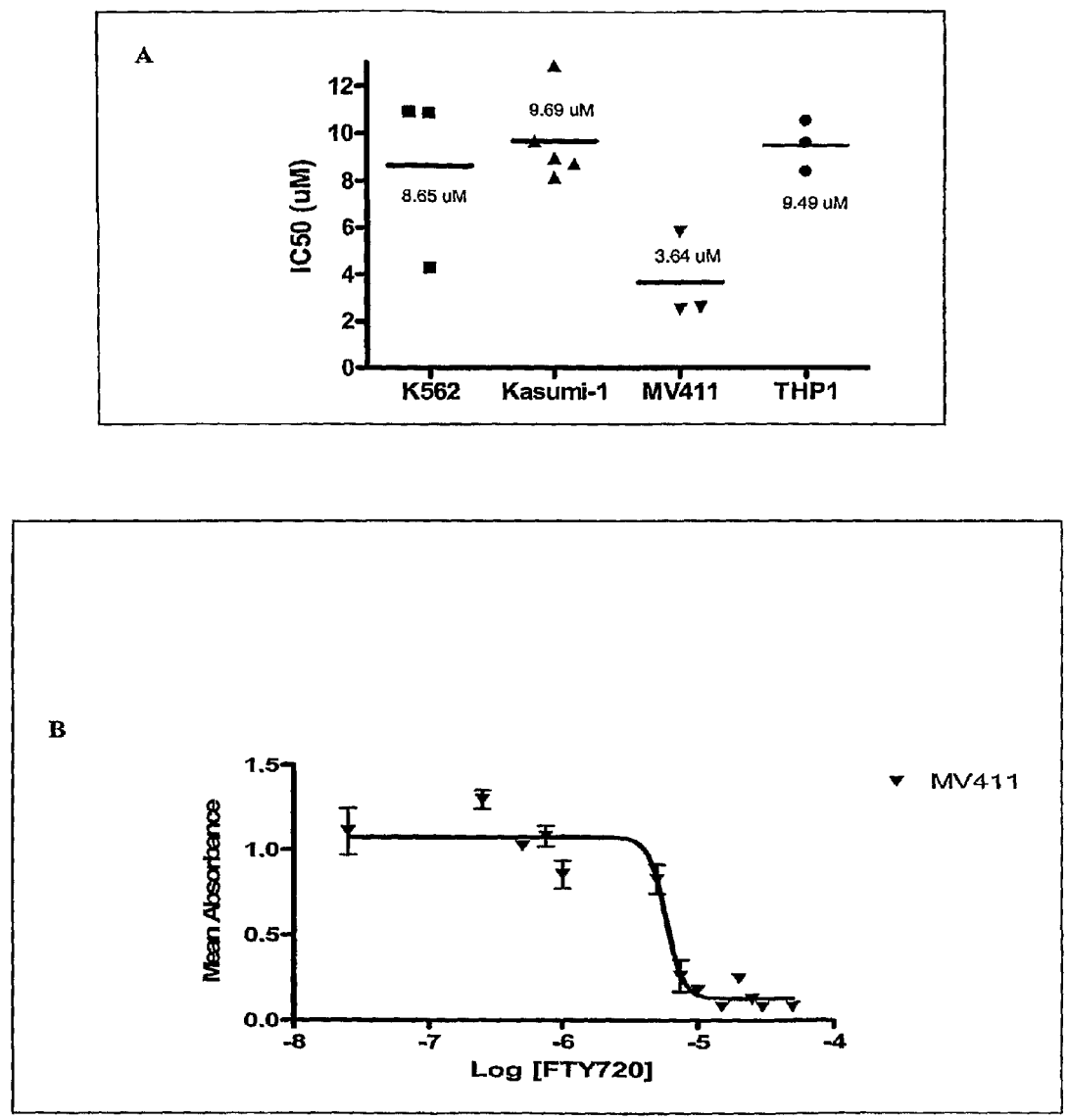
FIG. 9: FTY720 inhibits proliferation of several acute myeloid leukemia (AML) cell lines. Cell cultures were exposed for 48 hours to vehicle control and increasing concentrations of FTY720, and subsequently subjected to MTS assay per manufacturer's instructions. Mean concentrations (FIG. 9A) at which proliferation was inhibited by 50% (IC50) and representative dose curves (FIG. 9B) are shown.

FTY720 inhibits proliferation of several acute myeloid leukemia (AML) cell lines. Cell cultures were exposed for 48 hours to vehicle control and increasing concentrations of FTY720, and subsequently subjected to MTS assay per manufacturer's instructions. Mean concentrations (FIG. 9A) at which proliferation was inhibited by 50% (IC50) and representative dose curves (FIG. 9B) are shown.

Figure 10:
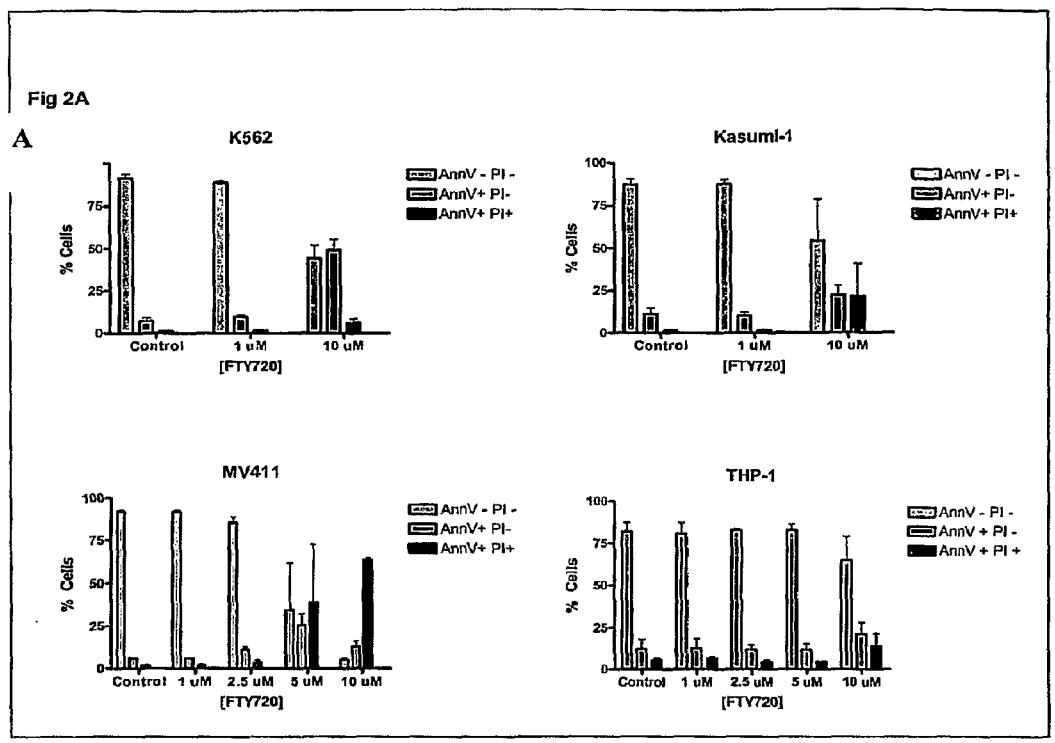
FIG. 10: FTY720 induces apoptosis in AML cell lines. Cell cultures were exposed to vehicle control and increasing doses of FTY720 for 48 hours. Cells were then stained with Annexin V (AnnV) and propidium iodide (PI), and analyzed using routine flow cytometry. Percentage of viable cells (AnnV− PI−), cells undergoing apoptosis (AnnV+ PI−), and necrotic cells (AnnV+ PI+) are represented for each cell line studied in FIG. 10A. Representative plots for the MV411 cell line are shown in FIG. 10B.
Figure 10:
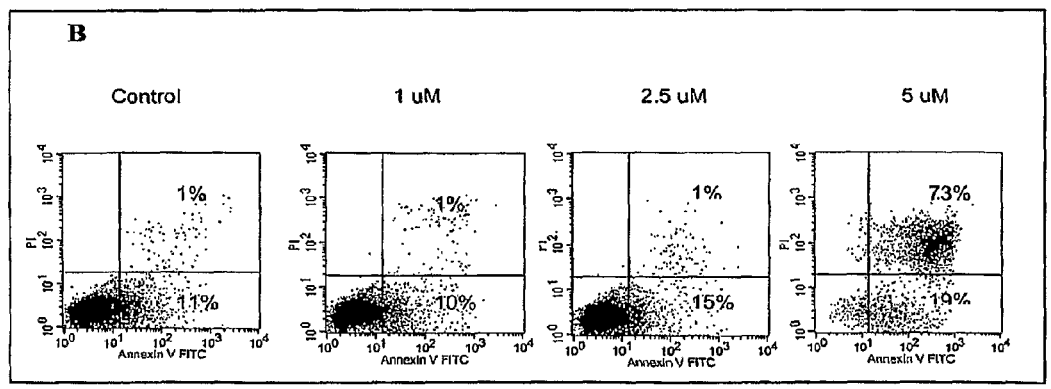

FTY720 induces apoptosis in AML cell lines. Cell cultures were exposed to vehicle control and increasing doses of FTY720 for 48 hours. Cells were then stained with Annexin V (AnnV) and propidium iodide (PI), and analyzed using routine flow cytometry. Percentage of viable cells (AnnV− PI−), cells undergoing apoptosis (AnnV+ PI−), and necrotic cells (AnnV+ PI+) are represented for each cell line studied in FIG. 10A. Representative plots for the MV411 cell line are shown in FIG. 10B.

FTY720 does not cause cell cycle arrest in AML cell lines. Cell suspensions were treated with vehicle control, 1 uM, and 10 uM FTY720 for 48 hours. After fixation in ethanol, samples were stained with propidium iodide, and assessed for DNA content. Percentage of cells in subG1, G1, S, and G2-M for each cell line are depicted (FIG. 11A) with representative plots below for MV411 (FIG. 11B). Although cell cycle arrest is not seen, induction of apoptosis is noted by the increased fraction of sub G1 with FTY720 treatment.

Figure 12:
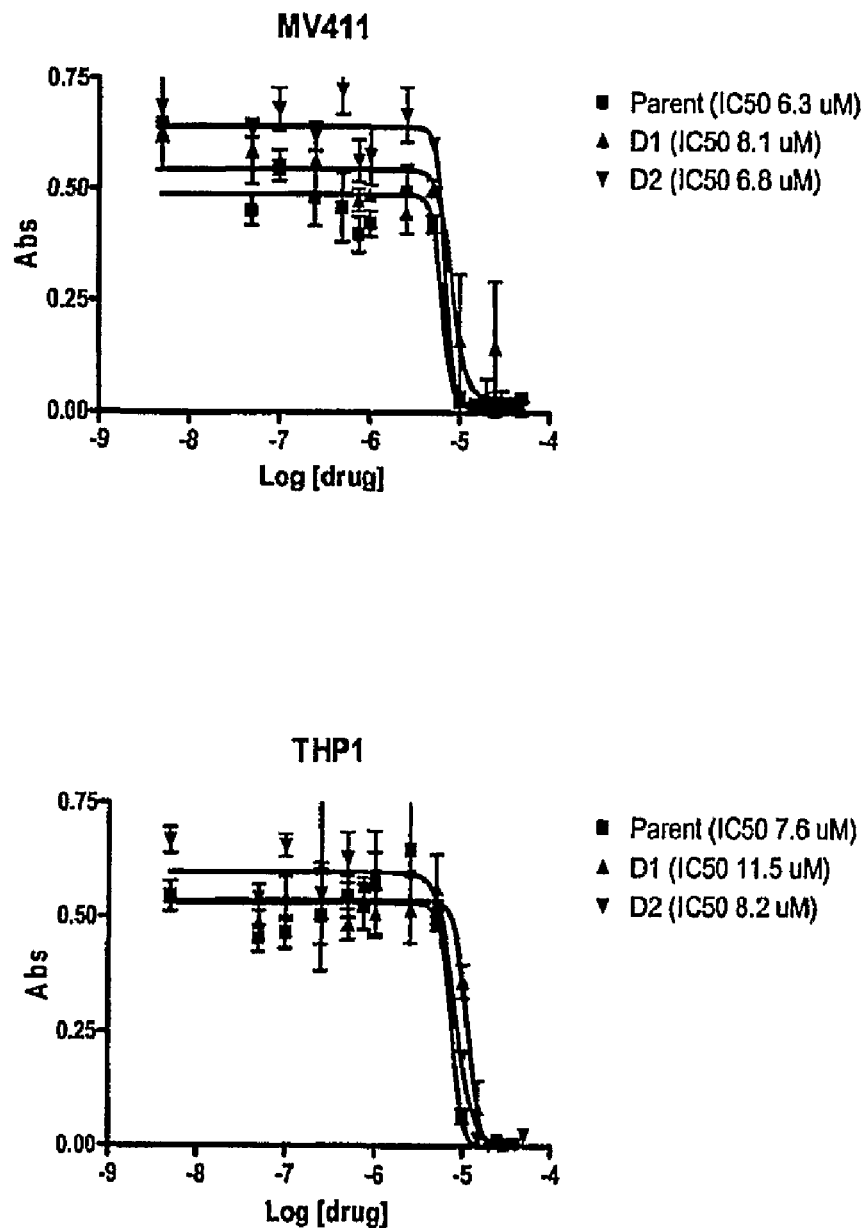
FIG. 12: FTY720 D2 derivative shows similar cytotoxicity to parent compound. Using MTS assay, inhibition of cell proliferation for various derivatives was examined. While D1 appears to be slightly less effective, AML cell lines show similar sensitivity to D2, a less immunosuppressive derivative.

FTY720 D2 derivative shows similar cytotoxicity to parent compound. Using MTS assay, inhibition of cell proliferation for various derivatives was examined. While D1 appears to be slightly less effective, AML cell lines show similar sensitivity to D2, a less immunosuppressive derivative (FIG. 12).

EXAMPLE 3

Over-expressed Cyclin D1 and constitutively phosphorylated Akt have been implicated in mantle cell lymphoma (MCL) pathogenesis. We describe here FTY720, an immunosuppressive agent currently in phase III studies, to mediate time- and dose-dependent apoptosis in primary MCL cells and cell lines. FTY720 treatment resulted in time dependent down modulation of Cyclin D1 and Akt protein levels, thus targeting two critical disease relevant molecules in mantle cell lymphoma. FTY720 induced apoptosis resulted in PARP processing and Mcl-1 down-modulation and was inhibited by pan caspase inhibitor, z-VAD-fmk. Consistent with the modulation of cyclin D1, FTY720 induced cell cycle deregulation associated with accumulation of cells in G0/G1 and G2/M phase of the cell cycle with concomitant decrease in S phase entry. These results provide the first evidence for a potential use for FTY720 in targeting Cyclin D1 and Akt molecules implicated in pathogenesis of mantel cell lymphoma.

Mantle cell lymphoma is an aggressive form of B cell malignancy characterized by abnormal accumulation of CD20+CD22+IgM+IgD+CD5+ B cells in lymph nodes, spleen, bone marrow and/or blood. Mantle cell lymphoma represents 6% of all non-Hodgkin's lymphomas and although treatment with chemotherapeutic agents is initially effective, virtually all patients relapse with median survival of 3 years. A variety of combination based therapies, including autologous stem cell transplant or targeted therapies such as rituximab, bortezomib, CCI779 and other therapies have been previously reviewed. The pathogenesis of the disease is attributed to constitutively active Ser/Thr kinase, Akt4, a survival pathway associated with defective phosphatase activity and up-regulation of Cyclin D1 associated with chromosomal translocation t(11;14)(q13;q32) between the IgH and Bcl-1 genes5. Deregulation of anti and pro-apoptotic proteins also have been implicated in this disease. Agents that target all of these pathways have potential use as immediate therapeutic medicine to MCL.

FTY720, [(2-Amino-2-3 propane 1,3-diol hydrochloride)], is a synthetic compound produced by modification of a natural immunosuppressant, ISP-1 that recently was demonstrated to exhibit in-vitro activity against multiple myeloma. FTY720 is currently in Phase III clinical trials as immunosuppressant for renal transplant rejection. We report here evidence for toxic effects of FTY720 targeting at down-modulation of Cyclin D1 and Akt, two critical targets implicated in pathogenesis of MCL. These data overall suggest that FTY720 might have promise as a therapeutic for the treatment of mantle cell lymphoma.

Materials and Methods

Primary MCL cells were isolated from PBMC (with informed patient consent under a protocol approved by IRB) as described before. All the MCL patients were identified as outlined by the World Health Organization (WHO) classification. Human mantle cell lymphoma patient cell lines (Mino and Jeko) were obtained from Dr. Raymond Lai. Primary cells or MCL cell lines were incubated in RPMI 1640 media, supplemented with 10%-20% heat-inactivated fetal bovine serum, 2 mM L-glutamine and penicillin (100 U/mL)/streptomycin (100 g/ml) at 37° C. in an atmosphere of 5% $CO_2$. FTY720 was synthesized as previously described. Toxicity was determined by flow cytometry using Annexin-V-FITC and Propidium Iodide (PI) staining. Apoptotic cells were identified as Annexin-V+ and/or PI+ cells. Cells excluding both FITC and PI were considered viable. Western Blotting was performed as described previously using indicated antibodies. The PARP (Ab-2) and Caspase 9 antibodies were purchased from Oncogene/Calbiochem/EMD Biosciences (San Diego, Calif.). Cyclin D1, Akt, Actin, Mcl-1, p-ERK, ERK and Bcl-2 were obtained from Santa Cruz biotech (Santa Cruz, Calif.).

Figure 13:
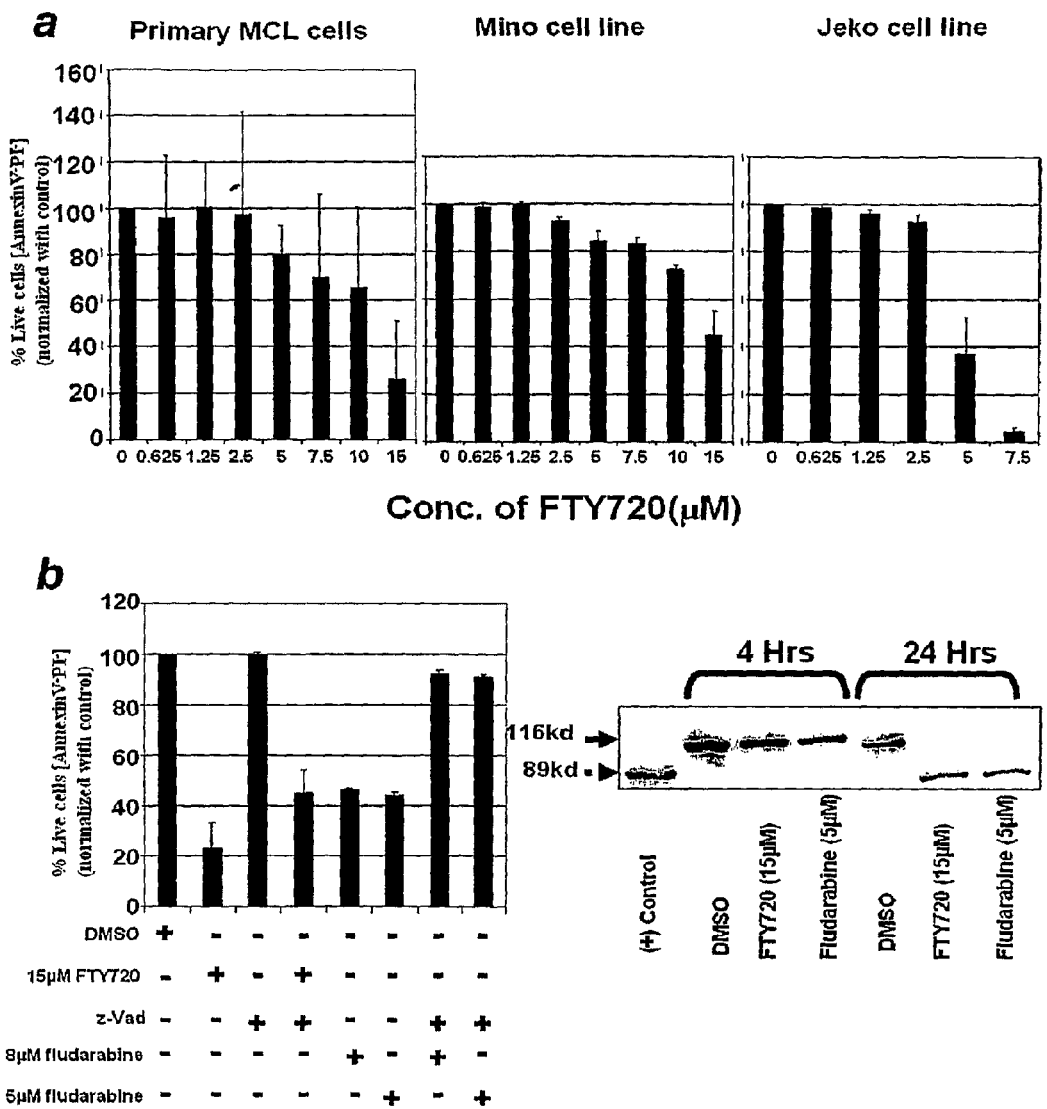
FIG. 13: FTY720 induced apoptosis in Mantle cell lymphoma cells through caspase activation dependent mechanism. Panel a: FTY720 induced apoptosis in MCL cells: Primary MCL cells ($2\times106$/ml), Jeko and Mino cells ($5\times105$) were treated with 0, 1.25, 5, 7.5, 10 and 15 μM FTY720 for 24 hrs. Cells were collected and stained with Annexin-V-FITC and Propidium Iodide. The cells were analyzed by flow cytometry. The live cells were identified by excluding FITC and PI staining. The Annexin V−/PI− cells normalized to vehicle controls are represented as % live cells. Panel b: FTY720 induced apoptosis is dependent on caspase activation. Mino cells ($5\times105$/ml) were treated with 15 μM FTY720 in the presence or absence of 150 μM z-Vad-fmk for 24 hrs. Left panel represents percentage of Annexin-V−/PI− viable cells+SD normalized to media control. Right panel shows western blot analysis of lysates at 4 hrs and 24 hrs post treatment with anti-PARP antibody. Lysates from UV treated cells were used as positive control for processed PARP.

FTY720 induces apoptosis in MCL Cell Lines and Primary Patient Samples: Incubation of primary MCL cells, Mino or Jeko MCL cell lines with increasing concentrations of FTY720 resulted in dose dependent decrease of viable cells (Annexin-V−/PI−) with concomitant increase in apoptotic (Annexin V+ and Annexin V+PI+) or dead cells (PI+ cells) (FIG. 13a and data not shown). IC50 values of FTY720 calculated using WinNolin sigmoid inhibitory model showed 10.67 μM, 4.46 μM and 11.86 μM in primary MCL, Jeko and Mino cells respectively. Several therapeutic agents, including fludarabine, chlorambucil, 2-chloro-2-deoxyadenosine and glucocorticoids, induce toxicity in B cell malignancies through activating caspases, the cysteine proteases of CED3/ICE family. Inhibition of these caspases results in abrogation of apoptosis mediated by the toxic stimuli. To determine if caspase activation is involved in FTY720-induced cytotoxicity in MCL, we pretreated Mino cells with 150 μM broad spectrum caspase inhibitor z-VAD-fmk. As shown in FIG. 13b, concentrations of z-VAD-fmk that resulted in ~50% reduction in fludarabine induced apoptosis also exhibited ~50% reduction in FTY720 induced apoptosis in Mino cells [fludarabine vs. fludarabine+z-VAD-fmk; $p<0.0001$, $n=3$; FTY720 vs. FTY720+z-VAD-fmk; $p<0.0001$, $n=3$]. Activation of caspases results in cleavage of key cellular proteins including poly-ADP-ribose polymerase (PARP). Consistent with the ability of z-VAD-fmk to rescue FTY720-induced apoptosis, Western Blotting analysis of lysates prepared from Mino cells 24 hrs post treatment with FTY720 showed PARP processing comparable to the levels seen with Fludarabine that has been shown to activate caspase cascade (FIG. 13b right panel).

FTY720 induced apoptosis is associated with down-modulation of Cyclin D1 and Akt. The pathogenesis of MCL is attributed to over-expression of Cyclin D1 protein. To determine if the FTY720 induced apoptosis is mediated through modulation of these targets relevant to the pathogenesis of the disease, we evaluated the effect of FTY720 on levels of Cyclin D1, p-Akt and Akt proteins by Wester Blotting analysis using specific antibodies in primary MCL cells and cell lines. Treatment of primary MCL cells with FTY720 resulted in time dependent down-regulation of Cyclin D1 protein, observed as early as 8 hrs post treatment (35%) that progressively increased to 70% by 24 hrs (2a-Left panel). Similar reduction in Cyclin D1 was also observed in Mino cell line, although with delayed kinetics with pronounced inhibition seen as early as 24 hrs with maximal inhibition bt 48 hrs post treatment (FIG. 14c). Phosphorylated Akt (p-Akt) has been implicated in MCL pathogenesis in primary cells from MCL patients4. Consistent with the modulation of Akt pathway in primary MCL, FTY720 also induced decrease in p-Akt. The decreased p-Akt is attributed to selective decrease in Akt protein levels observed by 24 hours (FIG. 14a right panel). Interestingly, FTY720 induced down regulation is selective to cyclin D1 and Akt and to a lesser extent Mcl-1 but not Bcl-2 or actin (FIG. 14b). The FTY720 induced down-regulation of Cyclin D1 and Akt indicated that FTY720 targets two of the most critical molecules associated with pathogenesis of MCL.

Deregulated cyclin D1 expression contributes to cell cycle defects in MCL cells. To determine if the FTY720 induced Cyclin D1 down modulation resulted in defects in cell cycle progression. Mino cells were treated with FTY720 for 12, 24 and 48 hrs and subjected to cell cycle analysis by flow cytometry. As shown in FIG. 14d, FTY720 treatment resulted in dose and time dependent decreased entry into S phase of the cell cycle Thus compared to vehicle control FTY720 treatment resulted in ~48% reduction in cells in S-phase. This decrease in S phase is entry is further reflected by accumulation of cells in G1 phase of the cell cycle.

Phosphorylated FTY720 has been shown to serve as a ligand for four of the five sphingosine-1-phosphate receptors (S1PRs). Binding of FTY720 accelerates homing of peripheral lymphocytes to lymph node and activation of S1PRs leads to extracellular signal-related kinase 1/2 (ERK1/2) phosphorylation. To determine if FTY720 influenced phosphorylation status of ERK-1, Mino cells were treated with FTY720 and the ERK1/2 phosphorylation status was analyzed by westernblot analysis using phospho ERK-1/2 and ERK1/2 antibodies. As shown in FIG. 14e, FTY720 induced ERK1/2 phosphorylation as early as 2 hrs post treatment that increased in time dependent manner with maximal phosphorylation seen as early as 4 hrs that was maintained as late as 10 hrs tested. The data suggests that FTY720 might activate S1P receptors and subsequently activating ERK. Similar FTY720 induced time dependent phosphorylation of ERK1/2 was also observed in Jeko cell line (Data not shown). FTY720 induced activation Ras-Raf-MAP kinase signaling pathway resulting in activation of serine/threonine kinase may contribute to ERK1/2 phosphorylation. Consistent with hypothesis ERK1/2 phosphorylation has been reported to occur in cells treated with Sphingosie 1-phosphate, that shares structural similarity to FTY72014. The role of FTY720 induced Erk1/2 phosphorylation in either toxicity, deregulation of the proteins such as Cyclin D1 or Akt and/or accumulation cells in G1 with concomitant decrease in S phase remains to be tested. Nevertheless these studies have identified Cyclin D1 and Akt proteins as two potential biomarkers for FTY720 responsiveness in MCL patient cells. In conclusion, these studies provide evidence for potential use of FTY720, as a potent agent targeted against deregulated Cyclin D1 and Akt in MCL.

The invention claimed is:

1. A method of treating a lymphoid malignancy in a subject, the method consisting of
    administering a therapeutically effective amount of 2-Amino-2-[2-(4-octylphenyl) ethyl]propane 1,3-diol hydrochloride or a pharmaceutically acceptable salt thereof and at least one of a pharmaceutically acceptable carrier, adjuvant, or diluent to a subject in need of such treatment.

2. The method of claim 1 wherein the subject has been diagnosed with a lymphoid malignancy selected from the group consisting of acute lymphoblastic leukemia (ALL), chronic lymphocytic leukemia (CLL), B-cell lymphoma, and mantle cell lymphoma (MCL).

3. The method of claim 1 wherein the subject is refractory to other treatments.

4. The method of claim 1 wherein the subject is a human subject.

5. A method of inducing apoptosis in lymphoid malignancies in a subject, the method consisting of
    administering a therapeutically effective amount of 2-Amino-2-[2-(4-octylphenyl) ethyl]propane 1,3-diol hydrochloride or a pharmaceutically acceptable salt thereof and at least one of a pharmaceutically acceptable carrier, adjuvant, or diluent to a subject in need of such treatment.

6. The method of claim 5 wherein the lymphoid malignancy is selected from the group consisting of acute lymphoblastic leukemia (ALL), chronic lymphocytic leukemia (CLL), B-cell lymphoma, and mantle cell lymphoma (MCL).

7. The method of claim 5 wherein the subject is a human subject.

8. The method of claim 2 wherein the subject is refractory to other treatments.

9. The method of claim 8 wherein the subject is a human subject.

10. The method of claim 2 wherein the subject is a human subject.

11. The method of claim 6 wherein the subject is a human subject.

* * * * *